US006916843B1

(12) United States Patent  (10) Patent No.: US 6,916,843 B1
Liao et al.  (45) Date of Patent: Jul. 12, 2005

(54) ANTI-INFLAMMATORY ACTIONS OF CYTOCHROME P450 EXPOXYGENASE-DERIVED EICOSANOIDS

(75) Inventors: James K. Liao, Weston, MA (US); Darryl Zeldin, Chapel Hill, NC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 141 days.

(21) Appl. No.: 09/634,369

(22) Filed: Aug. 9, 2000

Related U.S. Application Data

(60) Provisional application No. 60/148,434, filed on Aug. 11, 1999.

(51) Int. Cl.[7] ............................................. A61K 31/335
(52) U.S. Cl. ...................................... 514/449; 514/475
(58) Field of Search ................................ 514/449, 475

(56) References Cited

U.S. PATENT DOCUMENTS

| | | | |
|---|---|---|---|
| 5,102,670 A | | 4/1992 | Abraham et al. |
| 5,334,736 A | | 8/1994 | Sun et al. |
| 5,593,990 A | * | 1/1997 | D'Amato .................. 514/235.2 |
| 5,834,293 A | | 11/1998 | Capdevila et al. |
| 5,925,375 A | | 7/1999 | Lenk et al. |
| 5,955,496 A | | 9/1999 | Hammock et al. |

FOREIGN PATENT DOCUMENTS

| | | |
|---|---|---|
| WO | WO 94/01139 | 1/1994 |
| WO | WO 98/06261 | 2/1998 |
| WO | WO 99/05299 | 2/1999 |

OTHER PUBLICATIONS

Node et al., Journal of the American College of Cardiology, Feb. 1999, vol. 33, No. 2 Suppl. A, pp. 2A.*
Ala et al., 37 Agents & Actions. 134–139 (1992).
Biegelsen et al., 10 Coron. Artery Dis. 241–56 (1999).
Blanc et al., 19 Liver 42–49 (1999).
Brown et al., 68 Methods in Enzymology 109–151 (1979).
Campbell et al., 78 Circ. Res. 415–423 (1996).
Casey & Seabra, 271 J. Biol. Chem. 5289–92 (1996).
Chen et al. 274(8) J. Biol. Chem. 4764–9(1999).
Corey et al., 102 J. Am. Chem. Soc. 1433–1435 (1980).
DeCaterina et al., 96 J. Clin. Invest. 60–68 (1995).
Dzau et al., 18(SupplIII) Hypertension. 1II115–III121 (1991).
Falck et al., 25 Tetrahedron Lett. 1755–1756 (1982).
Gething & Sambrook, 293 Nature 620–625 (1981).
Giraldez et al., 272 J. Biol. Chem. 21420–21426 (1997).
Green et al., 126 Anal. Biochem. 131–138 (1982).
Gyllenhammar et al., 97 J. Immunol. Methods. 209–213 (1987).
Hess et al., 25 Stroke. 1463–1467 (1994).
International Search Report, issued Oct. 13, 2000.

Lefer et al., 33 Annu. Rev. Pharmacol. Toxicol 71–90 (1993).
Li et al., 41 Cardiovasc. Res. 109–115 (1999).
Liao et al., 44 Clin. Chem. 1799–1808 (1998).
Marti et al., 156 Am. J. Pathol. 965–976 (2000).
Mathews et al., 16 Free Radic. Biol. Med. 763–70 (1994).
May & Ghosh, 284(5412) Science 271–3 (1999).
Mehta et al., 257 Am. J. Physiol. H1240–H1246 (1989).
Mehta et al., 5 J. Myocard. Ischemia. 31–41 (1993).
Merrifield, 85 J. Amer. Chem. Soc. 2149–2154 (1963).
Meyer et al., 12 Can. J. Cardiol. 930–934 (1996).
Miyake et al., 114 J. Cell Biol. 557–565 (1991).
Morisseau et al., 96 Proc. Natl. Acad. Sci. USA 8849–8854 (1999).
Morrow & Roberts, 300 Methods Enzymol. 3–12 (1999).
Morrow et al., 87 Proc. Natl. Acad. Sci. USA 9383–9387 (1990).
Node et al., 285 Science 1276–1279 (1999).
Oltman et al., 83 Circ. Res. 932–939 (1998).
Oltman et al., Database BIOSIS Accession No. 515821.
Palombella et al., 78 Cell 773–785 (1994).
Ramos et al., 84 Circ. Res. 1237–1244 (1999).
Reilly et al., 96 Circulation. 3314–3320 (1997).
Rosolowsky et al., 1299 Biochim. Biophys. Acta. 267 (1996).
Russell et al., 278 Am. J. Physiol. Gastrointest. Liver Physiol. G878–G885 (2000).
Samarasinghe et al., 24 Heptatology. 1230–1237 (1996).
Scarborough et al., 31(1) Drug Metab Rev. 205–34.
Schweer et al., 32 J. Mass Spectrom. 1362–1370 (1997).
Shin et al., 271 J. Biol. Chem. 271: 11317–11324 (1996).
Stemmer et al., 164 Gene. 49–53 (1995).
Tan et al., 17 Eur. J. Vasc. Endovasc. Surg. 373–89 (1999).
VanRollins et al., 34 J. Lipid Res. 1931–1942 (1993).
Wu et al., 271 (7) J. Biol. Chem. 3460–8 (1996).
Wu, et al., 272 J. Biol. Chem. 12551–9 (1997).
Yang et al., 274 Am. J. Physiol. H1955–H1961 (1998).
Yang et al., 83 Circ. Res. 552–559 (1998).
Yu et al., 57(5) Mol. Pharmacol. 1011–20 (2000).
Zeldin et al., 50(5) Mol. Pharmacol 1111–7 (1996).
Zeldin et al., 51 Mol. Pharm. 931–943 (1997).

* cited by examiner

*Primary Examiner*—Raymond Henley, III
*Assistant Examiner*—C. Delacroix-Muirheid
(74) *Attorney, Agent, or Firm*—Klarquist Sparkman, LLP

(57) ABSTRACT

Epoxyeicosatrienoic acids (EETs) are products of cytocrome P450 epoxygenases that have vasodilatory properties similar to endotheilum-derived hyperpolarizing factor (EDHF). The cytochrome P450 isoform CYP2J2 was cloned and identified as a source of EETs in human endothelial cells. Physiological concentrations of EETs or overexpression of CYP2J2 decreased cytolcine-induced endothelial cell adhesion molecule expression and prevented subsequent leukocyte adhesion to the vascular wall by a mechanism involving inhibition of transcription factor NF-κB and IκB kinase (IKK). The inhibitory effects of EETs were independent of their membrane hyporpolarizing effects suggesting that these molecules play an important non-vasodilatory role in vascular inflammation.

25 Claims, 15 Drawing Sheets

Pretreatment 1 h with RKB or KMR

TNF-alpha (10 ng/ml)
24 h stimulation 1. no stimulation
2. TNF-alpha (10 ng/ml)
3. TNF+RKB (1nM)
4. TNF+RKB (10 nM)
5. TNF+RKB (100 nM)
6. TNF+RKB (1 micro M)
7. RKB (100 nM)
8. TNF+KMR (1nM)
9. TNF+KMR (10 nM)
10. TNF+KMR (100 nM)
11. TNF+KMR (1 microM)
12. KMR (100 nM)

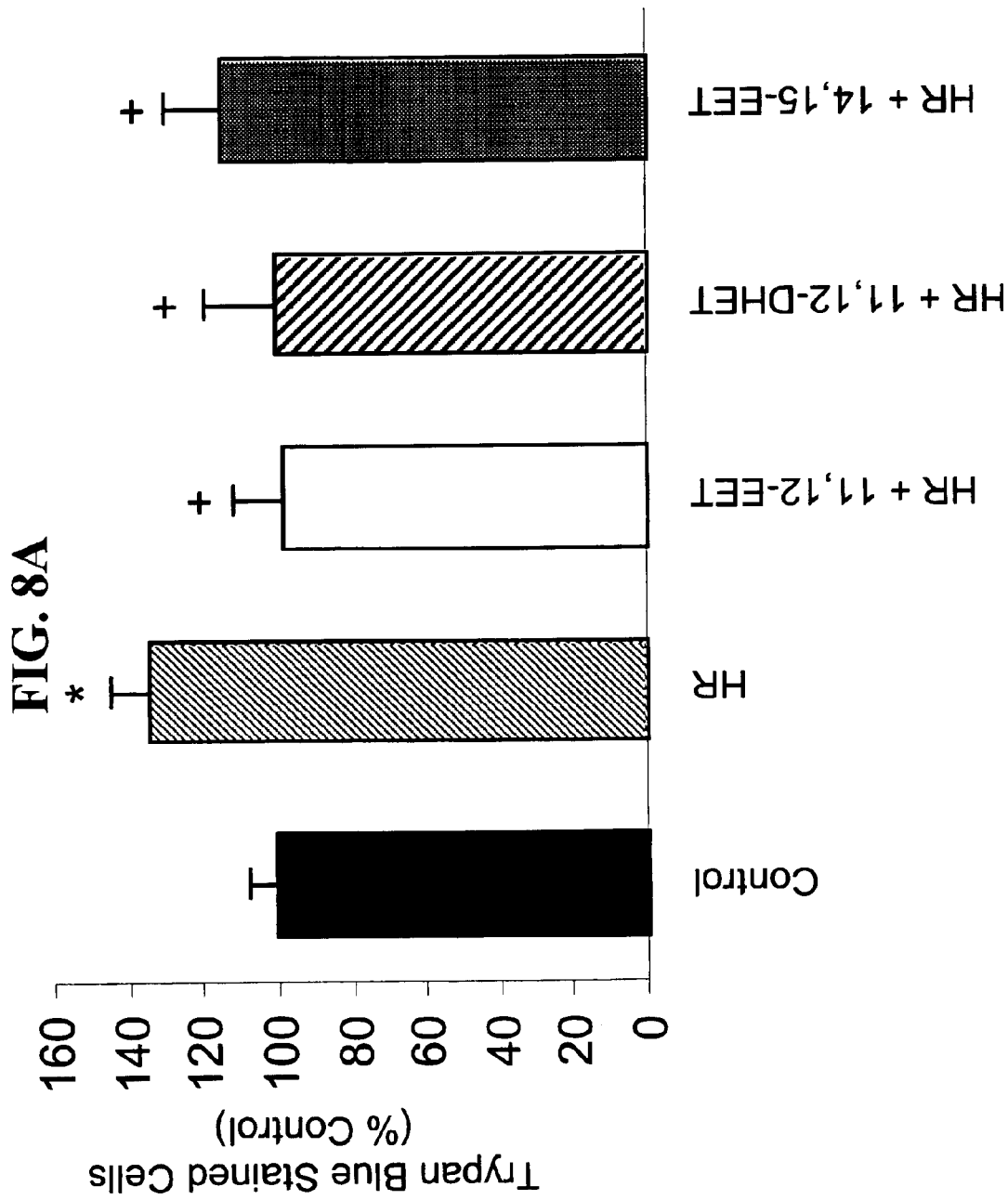

RKB-V-284-24

KMR-IV-87-27

SEQUENCE LISTING

<160> NUMBER OF SEQ ID NOS: 4

<210> SEQ ID NO 1
<211> LENGTH: 1020
<212> TYPE: DNA
<213> ORGANISM: Homo sapiens
<220> FEATURE:
<221> NAME/KEY: CDS
<222> LOCATION: (1)..(1020)
<223> OTHER INFORMATION:

<400> SEQUENCE: 1

```
gct gac ttt ctc aaa aga cgg cgc cca aag aac tac ccg ccg ggg ccc        48
Ala Asp Phe Leu Lys Arg Arg Arg Pro Lys Asn Tyr Pro Pro Gly Pro
1               5                   10                  15 tgg cgc ttg ccc ttc ctt ggc aac ttc ttc ctt gtg gac ttc gag cag        96
Trp Arg Leu Pro Phe Leu Gly Asn Phe Phe Leu Val Asp Phe Glu Gln
                20                  25                  30 tcg cac ctg gag gtt cag ctg ttt gtg aag aaa tat ggg aac ctt ttt       144
Ser His Leu Glu Val Gln Leu Phe Val Lys Lys Tyr Gly Asn Leu Phe
            35                  40                  45 agc ttg gag ctt ggt gac ata tct gca gtt ctt att act ggc ttg ccc       192
Ser Leu Glu Leu Gly Asp Ile Ser Ala Val Leu Ile Thr Gly Leu Pro
        50                  55                  60 tta atc aaa gaa gcc ctt atc cac atg gac caa aac ttt ggg aac cgc       240
Leu Ile Lys Glu Ala Leu Ile His Met Asp Gln Asn Phe Gly Asn Arg
65                  70                  75                  80 ccc gtg acc cct atg cga gaa cat atc ttt aag aaa aat gga ttg att       288
Pro Val Thr Pro Met Arg Glu His Ile Phe Lys Lys Asn Gly Leu Ile
                85                  90                  95 atg tca agt ggc cag gca tgg aag gag caa aga agg ttc act ctg aca       336
Met Ser Ser Gly Gln Ala Trp Lys Glu Gln Arg Arg Phe Thr Leu Thr
                100                 105                 110 gca cta agg aac ttt ggt tta gga aag aag ggc tta gag gaa cgc att       384
Ala Leu Arg Asn Phe Gly Leu Gly Lys Lys Gly Leu Glu Glu Arg Ile
            115                 120                 125 cag gag gag gcc caa cac ctc act gaa gca ata aaa gag gag aac gga       432
Gln Glu Glu Ala Gln His Leu Thr Glu Ala Ile Lys Glu Glu Asn Gly
        130                 135                 140 cag cct ttt gac cct cat ttc aag atc aac aat gca gtt tcc aat atc       480
Gln Pro Phe Asp Pro His Phe Lys Ile Asn Asn Ala Val Ser Asn Ile
145                 150                 155                 160
```

```
att tgc tcc atc acc ttc gga gaa cgc ttt gag tac cag gat agt tgg      528
Ile Cys Ser Ile Thr Phe Gly Glu Arg Phe Glu Tyr Gln Asp Ser Trp
            165                 170                 175 ttt cag cag ctg ctg aag tta cta gat gaa gtc aca tac ttg gag gct      576
Phe Gln Gln Leu Leu Lys Leu Leu Asp Glu Val Thr Tyr Leu Glu Ala
            180                 185                 190 tca aag aca tgc cag ctc tac aat gtc ttt cca tgg ata atg aaa ttc      624
Ser Lys Thr Cys Gln Leu Tyr Asn Val Phe Pro Trp Ile Met Lys Phe
            195                 200                 205 ctg cct gga ccc cac caa act ctc ttc agc aac tgg aaa aaa ctg aaa      672
Leu Pro Gly Pro His Gln Thr Leu Phe Ser Asn Trp Lys Lys Leu Lys
210                 215                 220 ttg ttt gtt tct cat atg att gac aaa cac aga aag gat tgg aat cct      720
Leu Phe Val Ser His Met Ile Asp Lys His Arg Lys Asp Trp Asn Pro
225                 230                 235                 240 gca gaa aca aga gac ttt att gat gct tac ctt aaa gaa atg tca aag      768
Ala Glu Thr Arg Asp Phe Ile Asp Ala Tyr Leu Lys Glu Met Ser Lys
            245                 250                 255 cac aca ggc aat cct act tca agt ttc cat gaa gaa aac ctc atc tgc      816
His Thr Gly Asn Pro Thr Ser Ser Phe His Glu Glu Asn Leu Ile Cys
            260                 265                 270 agc acc ctg gac ctc ttc ttt gcc gga acc gag aca act tcc aca act      864
Ser Thr Leu Asp Leu Phe Phe Ala Gly Thr Glu Thr Thr Ser Thr Thr
            275                 280                 285 ctg cga tgg gct ctg ctt tat atg gcc ctc tac cca gaa atc caa gaa      912
Leu Arg Trp Ala Leu Leu Tyr Met Ala Leu Tyr Pro Glu Ile Gln Glu
            290                 295                 300 aaa gta caa gtc gag att gac aga gtg att ggc cag ggg cag cag ccg      960
Lys Val Gln Val Glu Ile Asp Arg Val Ile Gly Gln Gly Gln Gln Pro
305                 310                 315                 320 agc aca gcc gcc cgg gag tcc atg ccc tac acc aat gct gtc atc cat     1008
Ser Thr Ala Ala Arg Glu Ser Met Pro Tyr Thr Asn Ala Val Ile His
            325                 330                 335 gag gtg cag agt                                                     1020
Glu Val Gln Ser
            340

<210> SEQ ID NO 2
<211> LENGTH: 340
<212> TYPE: PRT
<213> ORGANISM: Homo sapiens

<400> SEQUENCE: 2

Ala Asp Phe Leu Lys Arg Arg Pro Lys Asn Tyr Pro Pro Gly Pro
1               5                   10                  15

Trp Arg Leu Pro Phe Leu Gly Asn Phe Phe Leu Val Asp Phe Glu Gln
            20                  25                  30

Ser His Leu Glu Val Gln Leu Phe Val Lys Lys Tyr Gly Asn Leu Phe
        35                  40                  45

Ser Leu Glu Leu Gly Asp Ile Ser Ala Val Leu Ile Thr Gly Leu Pro
    50                  55                  60

Leu Ile Lys Glu Ala Leu Ile His Met Asp Gln Asn Phe Gly Asn Arg
65                  70                  75                  80

Pro Val Thr Pro Met Arg Glu His Ile Phe Lys Lys Asn Gly Leu Ile
                85                  90                  95

Met Ser Ser Gly Gln Ala Trp Lys Glu Gln Arg Arg Phe Thr Leu Thr
            100                 105                 110

Ala Leu Arg Asn Phe Gly Leu Gly Lys Lys Gly Leu Glu Glu Arg Ile
```

-continued

```
                    115                 120                 125
Gln Glu Glu Ala Gln His Leu Thr Glu Ala Ile Lys Glu Glu Asn Gly
        130                 135                 140

Gln Pro Phe Asp Pro His Phe Lys Ile Asn Asn Ala Val Ser Asn Ile
145                 150                 155                 160

Ile Cys Ser Ile Thr Phe Gly Glu Arg Phe Glu Tyr Gln Asp Ser Trp
                165                 170                 175

Phe Gln Gln Leu Leu Lys Leu Leu Asp Glu Val Thr Tyr Leu Glu Ala
                180                 185                 190

Ser Lys Thr Cys Gln Leu Tyr Asn Val Phe Pro Trp Ile Met Lys Phe
        195                 200                 205

Leu Pro Gly Pro His Gln Thr Leu Phe Ser Asn Trp Lys Lys Leu Lys
    210                 215                 220

Leu Phe Val Ser His Met Ile Asp Lys His Arg Lys Asp Trp Asn Pro
225                 230                 235                 240

Ala Glu Thr Arg Asp Phe Ile Asp Ala Tyr Leu Lys Glu Met Ser Lys
                245                 250                 255

His Thr Gly Asn Pro Thr Ser Ser Phe His Glu Glu Asn Leu Ile Cys
                260                 265                 270

Ser Thr Leu Asp Leu Phe Phe Ala Gly Thr Glu Thr Thr Ser Thr Thr
        275                 280                 285

Leu Arg Trp Ala Leu Leu Tyr Met Ala Leu Tyr Pro Glu Ile Gln Glu
    290                 295                 300

Lys Val Gln Val Glu Ile Asp Arg Val Ile Gly Gln Gly Gln Gln Pro
305                 310                 315                 320

Ser Thr Ala Ala Arg Glu Ser Met Pro Tyr Thr Asn Ala Val Ile His
                325                 330                 335

Glu Val Gln Ser
            340

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
gctgactttc tcaaaagacg                                                    20

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
ctctgcacct catggatgac                                                    20
```

ANTI-INFLAMMATORY ACTIONS OF CYTOCHROME P450 EXPOXYGENASE-DERIVED EICOSANOIDS

CLAIM OF PRIORITY

This application claims priority to U.S. provisional patent application No. 60/148,434, filed Aug. 11, 1999.

TECHNICAL FIELD OF THE INVENTION

This invention relates generally to compositions and methods for treating inflammation.

BACKGROUND OF THE INVENTION

Oxidation of arachidonic acid (AA) generates a variety of biologically active mediators. Three distinct arachidonic acid metabolic pathways have been described. Of the three pathways, considerable attention has been paid to the products of the cyclooxygenase and lipoxygenase pathways; and therapeutic effects have been well described.

By contrast, much less attention has been paid to the products of the so-called "third pathway." Unlike the other two pathways, this pathway is mediated by cytochrome P450 monooxygenases and uses NADPH and molecular oxygen in a 1:1 stoichiometry.

The metabolism of arachidonic acid by cytochrome P450 monoxygenases leads to the formation of various biologically active eicosanoids. Three types of oxidative reactions are known to occur. First, olefin epoxidation (catalyzed by epoxygenases) gives rise to the epoxyeicosatrienoic acids (EETs). Four important EET regioisomers are [5,6]-EET, [8,9]-EET, [11,12]-EET, and [14,15]-EET. The EETs are hydrolyzed by epoxide hydrolases to form the corresponding dihydroxycicosatrienoic acids (DHETs). Second, omega terminal oxidation leads to the formation of omega terminal hydroxyeicosatetraenoic acids (HETEs). Third, allylic oxidation leads to the formation of midchain HETEs.

Several cytochrome P450 epoxygenases have been identified, including members of the CYP1A, CYP2B, CYP2C, CYP2E, and CYP2J subfamilies. Attention has recently been focused on proteins of the CYP2J subfamily. One particular isoform, CYP2J2, is highly expressed in human cardiac myocytes, where arachidonic acid is metabolized to s produce EETs (Wu et al., 271 J. Biol. Chem. 12551 (1996)). CYP2J2 proteins are also found in epithelial cells in the airway and in the gut (Zeldin et al., 51 Mol. Pharm. 931 (1997); Zeldin et al., 50 Mol. Pharm. 1111 (1996)). In contrast to the other P450 enzymes, CYP2J2 proteins are distributed uniformly along the length of the gut, in epithelial and non-epithelial cells. High levels of the CYP2J2 proteins are found in cells of the autonomic ganglia, epithelial cells, and intestinal smooth muscle cells. Several CYP2J homologues have been identified in animals including rat CYP2J3, rat CYP2J4, mouse CYP2J5 and mouse CYP2J6 (Zhang et al., 340 Arch. Biochem. Biophys. 270 (1997); Ma et al., 274 J. Biol. Chem. 17777 (1999)).

The EETs are considered to be potential candidates for endothelium-derived hyperpolarizing factor (EDHF) because they hyperpolarize and relax vascular smooth muscle cells by activating calcium-sensitive potassium ($K_{Ca}$) channels (Campbell et al., 78 Circ. Res. 415 (1996); Rosolowsky et al., 1299 Biochim. Biophys. Acta. 267 (1996). EDHF is the substance that produces the vascular smooth muscle hyperpolarization which cannot be explained by nitric oxide (NO; the so-called endothelium-derived relaxing factor; EDRF). In the coronary microcirculation, EDHF and not NO is the predominant mediator of endothelium-dependent relaxation. EETs increase coronary blood flow and protect the myocardium from ischemia-reperfusion injury (Wu et al., 272 J. Biol. Chem 12551 (1997); Oltman et al., 83 Circ. Res. 932 (1998)).

What is not known, however, is whether EETs have an additional therapeutic usefulness.

SUMMARY OF THE INVENTION

The invention is a composition and methods for treating or preventing inflammation, or of preventing cell death by hypoxia-reoxygenation, by administering a pharmaceutical composition to a subject. The composition contains a composition of matter, containing certain cytochrome P450-derived eicosanoids (EETs, EET metabolic products, EET and DHET analogs, and combinations thereof) in a pharmaceutically acceptable excipient. The EETs can be the [5,6]-EET, [8,9]-EET, [11,12]-EET, [14,15]-EET, or combinations thereof with particular anti-inflammatory effectiveness. The EET analogs, such as episulfide and sulfonamide derivatives, have longer bioavailability and potentially greater stability than the EETs in that they are resistant to oxidation and hydrolysis.

Unexpectedly, physiological concentrations of EETs were found to decrease endothelial cell adhesion molecule (VCAM-1) expression and prevent subsequent leukocyte adhesion to the vascular wall. The cellular mechanism of this inhibition involves second messenger systems, in particular the inhibition of transcription factor NF-κB and Inhibitor κB kinase (IKK). Administration of EETs inhibits the IKK enzyme, thereby inhibiting the NF-κB system. The NF-κB system is required for increased expression of adhesion molecules on endothelial cells in response to pro-inflammatory cytokines, such as tumor necrosis factor alpha (TNF-α), interleukin-1 (IL-1), and cellular adhesion molecules. The inhibitory effects of EET administration are independent of their membrane hyperpolarizing effects. Thus, EETs have a second, anti-inflammatory function in the vascular wall, independent of the membrane hyperpolarizing or vasodilatory effect.

These EET compositions are useful anti-inflammatory agents for treating or preventing atherosclerosis, other inflammatory or immunological conditions, and other conditions where inhibition of adhesion molecule expression may be desirable. The potential beneficiaries of the invention includes patients with vascular and nonvascular inflammatory disorders (such as atherosclerosis, vasculitis, connective tissue diseases including rheumatoid arthritis), and cancer. This invention could potentially replace or supplement current anti-inflammatory agents, such as anti-inflammatory peptides, steroids, and non-steroid anti-inflammatory agents.

Other EET compositions are useful in preventing cell death due to hypoxia reoxygenation. We show here that CYP2J2 protein levels are markedly reduced following exposure of endothelial cells to hypoxia-reoxygenation and that maintenance of CYP2J2 levels attenuates the cellular injury. Given that endothelial injury is an important early event in the development of the atherosclerotic plaque and is associated with myocardial dysfunction in ischemic heart disease, reduced CYP2J2 protein and/or activity should be involved in the pathogenesis of these cardiovascular disorders. Accordingly, the invention provides a method for treating cell death from hypoxia-reoxygenation, by administering a therapeutically effective amount of a composition of matter selected from the group consisting of EETs, epoxyeicosatrienoic acid metabolic products, epoxyeicosatrienoic acid and dihydroxyeicosatrienoic acid analogs, and combinations thereof to a subject. The invention also provides a method for treating hypoxia-reoxygenation, by administering a cytochrome P450 epoxygenase protein or a recombinant cytochrome P450 epoxygenase coding polynucleotide to a subject.

BRIEF DESCRIPTION OF THE DRAWINGS

FIG. 2A shows the effects of P450 epoxygenase-derived eicosanoids (100 nM) on endothelial cell VCAM-1 expression in response to TNF-α (10 ng/ml), IL-1α (10 µg/ml), or lipopolysaccharide (LPS; 10 ng/ml) after 24 hours. FIG. 2B shows the effects of [11,12]-EET (100 nM) on unstimulated (control) or TNF-α (10 ng/ml)-induced VCAM-1, E-selection, and ICAM-1 expression. The difference between treatment with TNF-α alone and in the presence of [11,12]-EET were statistically significant (*$p<0.05$, **$p<0.01$), OD, optical density. FIG. 2C shows the effect of [11,12]-EET (100 nM) or [14,15]-EET (100 nM) on bovine endothelial cells transiently transferred with a NF-κB heterologous promoter (VCAM-1 tandem κB sites×2) construct linked to a luciferase reporter gene (pκB.Luc). After stimulation with TNF-α (10 ng/ml) in the presence or absence of EET, promoter activity was determined relative to basal activity. *$p<0.01$ vs. TNF-α alone. FIG. 2D shows the effect of transfection with empty vector (pcDNA3.1) or CYP2J2 cDNA subcloned into pcDNA3.1 on TNF-α-induced VCAM-1 or heterologous κB promoter activity in the presence or absence of SKF525A (100 µM). *$p<0.01$ vs. TNF-α alone. **$p<0.01$ vs. TNF-α alone+CYP2J2.

(FIG. 7A) Cell number. (FIG. 7B) Trypan blue stained cells. (FIG. 7C) lactate dehydrogenase (LDH) release into the culture medium. Hypoxia-reoxygenation results in significantly fewer cells, more trypan blue stained cells and higher lactate dehydrogenase (LDH) release in GFP-transfected BAECs. The hypoxia-reoxygenation-induced changes in trypan blue stained cells and LDH release are significantly attenuated in CYP2J2-transfected BAECs. *$p<0.01$ vs. CYP2J2-transfected cells maintained under normoxic conditions; $^{++}p<0.01$ vs. GFP-transfected cells exposed to hypoxia-reoxygenation; N=19–24 in each group.

FIG. 8 shows the effect of synthetic arachidonic acid metabolites and epoxide hydrolase inhibitors on hypoxia-reoxygenation-induced cell injury in BAECs. (FIG. 8A) Addition of 1 µmol/L [11,12]-EET, [11,12]-DHET, or [14,15]-EET to BAECs 10 min prior to hypoxia significantly attenuates hypoxia-reoxygenation-induced cell injury as measured by the number of trypan blue stained cells. *$p<0.05$ vs. control; $^+p<0.05$ vs. hypoxia-reoxygenation; N=5 in each group.

FIG. 9 shows the effect of CYP2J2 transfection on cellular F$_2$-isoprostanes and superoxide anion production by BAECs.

FIG. 10 shows the effect of CYP2J2 transfection on eNOS expression, nitrite production and AT1 receptor expression in BAECs exposed to hypoxia-reoxygenation. Forty-eight hours after transfection of BAECs with either pcDNA3.1/GFP or pcDNA3.1/CYP2J2, cells were exposed to hypoxia-reoxygenation. eNOS expression, nitrite production and AT1 receptor expression were determined.

DETAILED DESCRIPTION OF THE INVENTION

Figure 1:
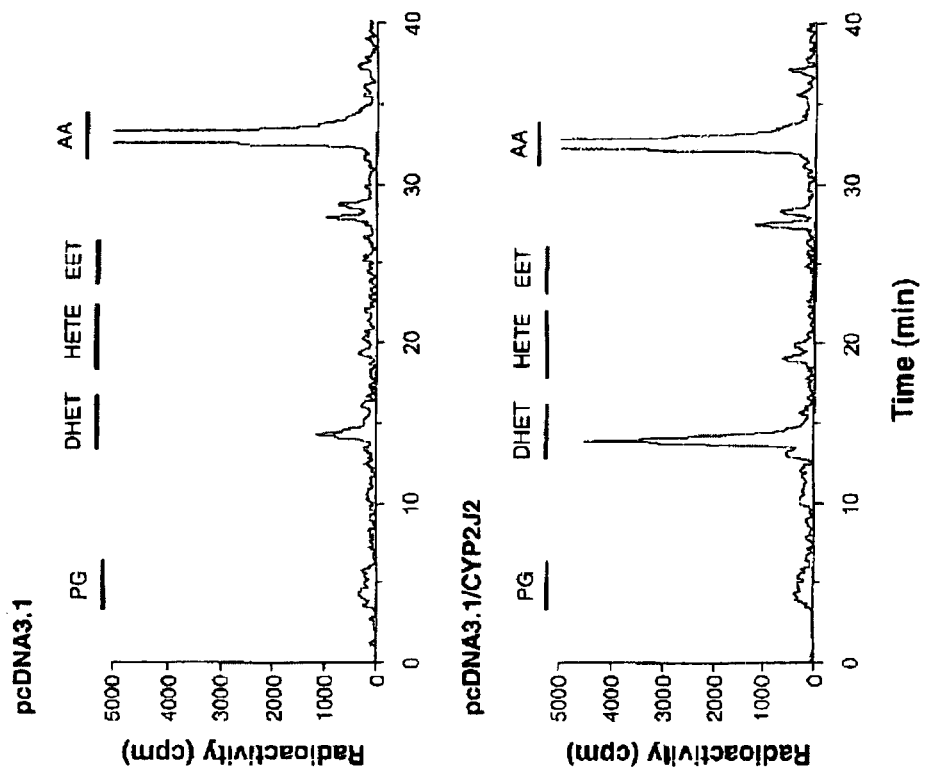
FIG. 1 is a reversed-phase HPLC chromatogram at metabolites generated during incubation of transfected endothelial cells with radiolabeled arachidonic acid. Endothelial cells were transfected with either empty vector (pcDNA3.1) or CYP2J2 expression vector CYP2J2/pcDNA3.1). The retention times of authentic standards are indicated by bars above the respective peaks. Ordinate: radioactivity in counts per minute (cpm.); Abscissa: time in minutes. Top panel: cells transfected with pcDNA3.1. Bottom panel: cells transfected with pcDNA3.1/CYP2J2.

This invention relates to method for treating inflammation and hypoxia-reoxygenation. In particular, the invention relates to:

(a) Cytochrome P450-derived eicosanoids, including epoxyeicosatrienoic acids, epoxyeicosatrienoic acid metabolic products, and epoxyeicosatrienoic acid and dihydroxyeicosatrienoic acid analogs, as novel therapeutics for the treatment or prevention of atherosclerosis, other inflammatory conditions, and other conditions where inhibition of adhesion molecule expression is desirable.

(b) Epoxyeicosatrienoic acids, including the [5,6]-EET, [8,9]-EET, and [11,12]-EET, as novel therapeutics for the treatment or prevention of atherosclerosis, other inflammatory conditions, and other conditions where inhibition of adhesion molecule expression is desirable, where the epoxyeicosatrienoic acids are active in inhibiting cytokine-induced upregulation of adhesion molecule expression in endothelial cells in vitro, preventing TNFα-induced expression of the adhesion molecule VCAM-1 in vivo, and preventing leukocyte adhesion to the vascular wall in an in vivo mouse vascular inflammation model.

(c) Epoxyeicosatrienoic acid metabolic products, including the dihydroxyeicosatrienoic acids (DHETs) [5,6]-DHET, [8,9]-DHET, [11,12]-DHET, and [14,15]-DHET, as novel therapeutics for the treatment or prevention of atherosclerosis, other inflammatory conditions, and other conditions where inhibition of adhesion molecule expression is desirable, where the DHETs are active in inhibiting cytokine-induced upregulation of adhesion molecule expression in endothelial cells in vitro.

(d) Relatively stable epoxyeicosatrienoic acid and dihydroxyeicosatrienoic acid analogs, including episulfide and sulfonamide derivatives, analogs in which one or more of the EET olefins are removed (i.e. epoxyeicosadienoic acids, epoxyeicosamonoenoic acids, epoxyeicosanoic acids), analogs in which the olefins are replaced with acetylene or cyclopropane groups, analogs in which the epoxide moiety is replaced with oxitane or furan rings, and heteroatom analogs, as novel therapeutics for the treatment or prevention of atherosclerosis, other inflammatory conditions, and other conditions where inhibition of adhesion molecule expression is desirable, where the epoxyeicosatrienoic acid and dihydroxyeicosatrienoic acid analogs are active in inhibiting adhesion molecule expression in vitro.

(e) Cytochrome P450 epoxygenase genes, including genes encoding members of the CYP1A, CYP2B, CYP2C, CYP2E, and CYP2J subfamily enzymes, particularly CYP2J2 which is expressed at high levels in human coronary vascular endothelial cells, wherein the cytochrome P450 epoxygenase genes can be overexpressed in a tissue-specific fashion as novel therapeutics for the treatment or prevention of atherosclerosis, other inflammatory conditions, and other conditions where inhibition of adhesion molecule expression is desirable, where the cytochrome P450 epoxygenase genes encode enzymes that catalyze the epoxygenation of arachidonic acid to epoxyeicosatrienoic acids and lead to the formation of epoxyeicosatrienoic acid metabolic products, including the dihydroxyeicosatrienoic acids.

(f) Cytochrome P450 epoxygenase proteins, including the CYP1A, CYP2B, CYP2C, CYP2E, and CYP2J enzymes, particularly CYP2J2, as novel therapeutics for the treatment or prevention of atherosclerosis, other inflammatory conditions, and other conditions where inhibition of adhesion molecule expression is desirable, where the cytochrome P450 epoxygenases catalyze the epoxygenation of arachidonic acid to epoxyeicosatrienoic acids and lead to the formation of epoxyeicosatrienoic acid metabolic products, including the dihydroxyeicosatrienoic acids.

(g) Epoxyeicosatrienoic acids, as regulators of an anti-inflammatory effect, which are present endogenously in vascular endothelial cells and present endogenously at higher levels in CYP2J2 transfected endothelial cells.

(h) Epoxide hydrolase inhibitors, including ureas, carbamides, and amides, as novel therapeutics for the treatment or prevention of atherosclerosis, other inflammatory conditions, and other conditions where inhibition of adhesion molecule expression is desirable, where these inhibitors prevent metabolism of endogenous or exogenously delivered epoxyeicosatrienoic acids to dihydroxyeicosatrienoic acids both in vivo and in vitro, resulting in increased epoxyeicosatrienoic acid levels, wherein these inhibitors potentiate the therapeutic effects of epoxyeicosatrienoic acids or their stable analogs.

(i) Eicosanoids as modulators of NF-κB and IκB kinase activity, where the epoxyeicosatrienoic acids and their stable analogs inhibit activity of these inflammatory regulators in vitro resulting in down-regulation of adhesion molecule expression on endothelial cells.

(j) A new functional role for CYP2J2 and its eicosanoid products in limiting endothelial injury following exposure to hypoxia-reoxygenation. We demonstrate that CYP2J2 protein levels are markedly reduced following exposure of endothelial cells to hypoxia-reoxygenation and that maintenance of CYP2J2 levels attenuates the cellular injury. Given that endothelial injury is an important early event in the development of the atherosclerotic plaque and is associated with myocardial dysfunction in ischemic heart disease (Liao et al., 44 Clin. Chem. 1799–1808 (1998), Biegelsen et al., 10 Coron. Artery Dis. 241–56 (1999), Lefer et al., 33 Annu. Rev. Pharmacol. Toxicol. 71–90 (1993)), we postulate that reduced CYP2J2 protein and/or activity are involved in the pathogenesis of these cardiovascular disorders.

The composition of matter of the invention is preferably used to treat inflammation or an immunological disorder, to prevent inflammation or an immunological disorder, inhibit expression of cell adhesion molecule, modulate NF-κB activity, or prevent cell death from hypoxia-reoxygenation in a mammal, e.g., a human. The composition of matter is useful for mammalian species other than humans, e.g., mouse, rat, rabbit, dog, cat cow, horse, and other mammals.

Inflammation. Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter referred to as cellular infiltration). The term "inflammation" thus includes the local reactions and resulting morphological changes, destruction or removal of injurious materials and activation of repair mechanisms. Inflammation can be part of the process by which animals heal themselves, but it can also occur in response to abnormal physiological stimuli and can cause problems in the body.

Inflammatory and immunological disorders which can be treated with the formulations of this invention include, without limitation: reperfusion injury, systemic inflammatory response syndrome (SIRS), myocardial infarction, adult respiratory distress syndrome (ARDS), vasculitis, post-traumatic shock, bum injuries, vaso-occlusive disorders, arthritic disorders, such as rheumatoid arthritis and gout, and auto-immune disorders, for example, systemic lupus erythematosus, juvenile diabetes, multiple sclerosis or Hashimoto's thyroiditis. Also, some inflammatory disorders are characterized by the abnormal activation of cells (e.g., platelets and neutrophils) in the blood, and by the subsequent adhesion of these cells to each other or to activated cells in the surrounding vascular endothelium.

Endothelial cells, for example vascular, plural, pericardial or abdominal endothelial cells, can be activated by pro-inflammatory cytokines, e.g., interleukin-1 (IL-1), tumor necrosis factor alpha (TNFα) or bacterial endotoxins (see, EXAMPLE 3). In like manner, blood cells, particularly neutrophils and platelets, can be activated by agents such as GM-CSF, bacterial endotoxins, bacterial chemoattractants, TNFα and the C5a component of complement. Activated cells have adhesion molecules on their surfaces by which they can adhere to each other. Activated and adhered cells can form clumps, which can clog small blood vessels such as those found in the lungs and heart, and thereby reduce blood flow to surrounding tissue. The activated cells can also adhere to activated vascular endothelial cells; such adhesion can lead to subsequent degranulation of vascular endothelium, or to the release of mediators of cell damage, such as superoxide anion ($O_2^-$) and proteolytic enzymes. Following reperfusion of occluded blood vessels, or incidental to surgery in which blood flow is temporarily stopped, surrounding endothelial cells, as well as downstream ischemic tissue, can be damaged. There can even be further damage to nearby endothelial cells when the occlusion is cleared. Such damaged cells can in turn induce activation in neutrophils and platelets after restoration of blood flow to the affected areas.

These inflammatory disorders are all within the scope of the invention.

Pharmaceutical composition and method of administration. The terms "treating," "treatment," and the like are used herein to mean obtaining a desired pharmacological or physiologic effect. The effect can be prophylactic in terms of completely or partially preventing a disorder or sign or symptom thereof, or can be therapeutic in terms of a partial or complete cure for a disorder and/or adverse effect attributable to the disorder. "Treating" as used herein covers any treatment and includes: (a) preventing an inflammatory disorder from occurring in a subject that can be predisposed to the disorder, but has not yet been diagnosed; (b) inhibiting the inflammatory disorder, i.e., arresting its development; or (c) relieving or ameliorating the inflammatory disorder.

The pharmaceutical composition can be administered in a variety of ways, orally, topically, parenterally e.g. subcutaneously, intraperitoneally, by viral infection, intravascularly, etc. Depending upon the manner of introduction, the pharmaceutical composition can be formulated in a variety of ways. In one example, the administration is by continuous intra-arterial infusion (see, EXAMPLE 5).

An "effective amount" or "therapeutically effective amount" of the pharmaceutical composition is the amount sufficient to obtain the desired physiological effect, e.g., treatment of inflammation. The amount of the EET administered is selected with regard to consideration of the subject's age, weight, sex, general physical condition and the like. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

Generally, the effective amount of the EET or EET metabolite is at least about $10^{-12}$ g of the metabolite per kg of body weight of the recipient. Typically, the effective amount is any amount from about $10^{-12}$ g of the metabolite per kg of body weight of the animal to about $10^{-3}$ g per kg, with a typical effective amount of about $10^{-6}$ g of the metabolite per kg of body weight. The amount of EET in the pharmaceutical formulation can vary, such that the resulting concentration present in the vascular endothelium is from, in the arteries, at an $EC_{50}$ of 1 μM (see, Rosolowsky et al., 1299 Biochim. Biophys. Acta. 267 (1996)) and Campbell et al., 78 Circ. Res. 415 (1996) for guidance as to the effective vasodilatory amounts), to in the arterioles, at an $EC_{50}$ of 0.1 nM (see, Oltman et al., 83 Circ. Res. 932 (1998) also for guidance as to the effective vasodilatory amounts). The preferred anti-inflammatory level for the pharmaceutical composition is 1–100 nM EET (see, EXAMPLE 3), with a common amount administered being 100 nM (see, FIG. 2). Alternatively, the method of administration can be at continuous intra-arterial infusion of [11,12]-EET (100 ng/kg/min) (see, FIG. 3).

The amount of the EET required for anti-inflammatory effect may vary with the particular EET used. As shown in EXAMPLE 3, [11,12]-EET is the most effective anti-inflammatory agent, followed by [8,9]-EET, [5,6]-EET, and [11,12]-DHET. Interestingly, [14,15]-EET, did not inhibit cell adhesion molecule expression, indicating differential bioactivity of specific EET regioisomers for the anti-inflammatory effects of particular EET (see, EXAMPLE 3).

The term EET "analog" includes compounds with structural substitutions or alterations in an EET, particularly in [11,12]-EET. In addition to the episulfide and sulfonamide derivatives, structural analogs include analogs in which one or more of the EET olefins are removed (i.e. epoxyeicosadienoic acids, epoxyeicosamonoenoic acids, epoxyeicosanoic acids), analogs in which the olefins are replaced with acetylene or cyclopropane groups, analogs in which the epoxide moiety is replaced with oxitane or furan rings, and heteroatom analogs. These compounds are "relatively stable" as compared with the unmodified EET, because the compounds are more resistant than EETs to endogenous epoxide hydrolases, endogenous oxidases, and chemical breakdown.

Excipient and additional agents. The pharmaceutical composition generally has a pharmaceutical carrier selected on the basis of the chosen route of administration and standard pharmaceutical practice. The pharmaceutical composition can further comprise suitable, i.e., physiologically acceptable, carriers (preferably for the preparation of injection solutions) and further additives as usually applied in the art (stabilizers, preservatives, etc.), as well as additional drugs. Such a carrier includes but is not limited to saline, buffered saline, dextrose, water, glycerol, ethanol, and combinations thereof. The formulation should suit the mode of administration. Suitable pharmaceutical carriers are described in the most recent edition of *Remington's Pharmaceutical Sciences*, a standard reference text in this field of art. For example, a parenteral composition suitable for administration by injection is prepared by dissolving 1.5% by weight of active ingredient in 0.9% sodium chloride solution. The preparation of these pharmaceutically acceptable compositions, having appropriate pH isotonicity, stability and other conventional characteristics is within the skill of the art.

The pharmaceutical composition can be administered using liposomes, using the methods described by U.S. Pat. No. 5,925,375, incorporated herein by reference, which describes the therapeutic use of multilamellar liposomal prostaglandin formulations and shows how liposomal formulations can prolong the circulatory half-lives of arachidonic acid metabolites and can help avoid their deactivation.

The pharmaceutical composition or method of this invention can comprise administering an additional bioactive agent, for example, an additional anti-inflammation agent. This additional agent is typically selected by means, and for reasons, well understood by those in the medical art for reducing inflammation. The additional agent can be an anti-inflammatory peptide, for example an anti-inflammatory peptide produced by recombinant methods. For example, these peptide can be peptides that inhibit pro-inflammatory cytokine action, that block receptor tyrosine kinases in the signaling pathways of the inflammatory response, or that are inhibitors of matrix metalloproteinases. The additional agent can be a steroid (e.g., cortisone, prednisone) or a non-steroid anti-inflammatory agents, like asprin, ibuprofen (Motrin®, Advil®), naproxen (Naprosyn®), sulindac (Clinoril®), diclofenac (Voltaren®), piroxicarn (Feldene®), ketoprofen (Orudis®), diflunisal (Dolobid®), nabumetone (Relafen®), etodolac (Lodine®), oxaprozin (Daypro®), and indomethacin (Indocin®).

Additionally, an anti-oxidant agent can be administered with the pharmaceutical composition of the invention.

The pharmaceutical composition or method of this invention can comprise administering an epoxide hydrolase inhibitor. The inhibitor can be a urea, carbamidc, amide, or combinations thereof. Examples of epoxide hydrolase inhibitors includes trichloropropene oxide, 4-phenylchalone oxide, substituted chalcone oxides (1,3-diphenyl-2-oxiranyl propanones) and structural analogs, dicyclohexylurea, etc. These inhibitors prevent metabolism of endogenous or exogenous epoxyeicosatrienoic acids to dihydroxyeicosatrienoic acids both in vivo and in vitro, resulting in increased epoxyeicosatrienoic acid levels, wherein these inhibitors potentiate the therapeutic effects of epoxyeicosatrienoic acids or their stable analogs.

Administration of cytochrome P450 epoxygenase. A polynucleotide encoding the cytochrome P450 epoxygenase protein can be prepared by chemical synthesis methods or by recombinant techniques. Also, the cytochrome P450 epoxygenase can be further upregulated using techniques provided by Yu et al., 57(5) Mol. Pharmacol. 1011–20 (2000).

The term "recombinant" refers to the molecular biological technology for combining polynucleotides to produce useful biological products, and to the polynucleotides and peptides produced by this technology. The polynucleotide can be a recombinant construct (such as a vector or plasmid) which contains the polynucleotide encoding the cytochrome P450 epoxygenase under the operative control of polynucleotides encoding regulatory elements such as promoters, termination signals, and the like. "Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence which is transcribed and translated into a polypeptide. Two coding polynucleotides are "operably linked" if the linkage results in a continuously translatable sequence without alteration or interruption of the triplet reading frame. A polynucleotide is operably linked to a gene expression element if the linkage results in the proper function of that gene expression element to result in expression of cytochrome P450 epoxygenase coding sequence. "Transformation" is the insertion of an exogenous polynucleotide (i.e., a "transgene") into a host cell. The exogenous polynucleotide is integrated within the host genome. A polynucleotide is "capable of expressing" a cytochrome P450 epoxygenase if it contains nucleotide sequences which contain transcriptional and translational regulatory information and such sequences are "operably linked" to polynucleotide which encode the cytochrome P450 epoxygenase. A polynucleotide that encodes a peptide coding region can be then amplified, for example, by preparation in a bacterial vector, according to conventional methods, for example, described in the standard work Sambrook et al., *Molecular Cloning: A Laboratory Manual* (Cold Spring Harbor Press 1989).

The cytochrome P450 epoxygenase polynucleotide can be prepared conventionally by chemical synthesis techniques, such as described by Merrifield, 85 J. Amer. Chem. Soc. 2149–2154 (1963) and Stemmer et al, 164 Gene 49 (1995)). Synthetic genes, the in vitro or in vivo transcription and translation of which will result in the production of the CYP2J2 or other cytochrome P450 epoxygenase protein can be constructed by techniques well known in the art (see Brown et al., 68 Methods in Enzymology 109–151 (1979)). The cytochrome P450 epoxygenase coding polynucleotide can be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404). Determinations of the sequences for the polynucleotide coding region that codes for the cytochrome P450 epoxygenase protein can be performed using commercially available computer programs, such as DNA Strider and Wisconsin GCG. Owing to the natural degeneracy of the genetic code, the skilled artisan will recognize that a sizable yet definite number of DNA sequences can be constructed which encode the claimed peptides (see, Watson el al., *Molecular Biology of the Gene*, 436–437 (The Benjamin/ Cummings Publishing Co. 1987)).

Alternatively, systems for cloning and expressing cytochrome P450 epoxygenases include various microorganisms and cells that are well known in recombinant technology. The cytochrome P450 epoxygenase gene can be constructed using the polymerase chain reaction (PCR) methodology, as described in EXAMPLE 1. Suitable vectors are known and available from private and public laboratories and depositories and from commercial vendors. See, Sambrook et al., *Molecular Cloning: A Laboratory Manual* (Cold Spring Harbor Press 1989). See, also PCT International patent application WO 94/01139. These vectors permit infection of a subject's cells and expression of the synthetic gene sequence in vivo or expression of it as a peptide or fusion protein in vitro. Suitable non-pathogenic viruses that can be engineered to carry the cytochrome P450 epoxygenase gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. Host mammalian cells, such as Chinese Hamster ovary cells (CHO) or COS-1 cells, can be used. These hosts can be used in connection with poxvirus vectors, such as vaccinia or swinepox. The selection of other suitable host cells and methods for transformation, culture, amplification, screening and product production and purification can be performed by one of skill in the art by reference to known techniques (see, e.g., Gething & Sambrook, 293 Nature 620–625 (1981)).

Polynucleotide gene expression elements useful for the expression of cDNA encoding peptides include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Recipient cells capable of expressing the cytochrome P450 epoxygenase are then transfected. The transfected recipient cells are cultured under conditions that permit expression of the cytochrome P450 epoxygenase.

An effective amount of the vector expressing cytochrome P450 epoxygenase is generally determined by the physician in each case on the basis of factors normally considered by one skilled in the art to determine appropriate dosages, including the age, sex, and weight of the subject to be treated, the condition being treated, and the severity of the medical condition being treated. In EXAMPLE 1, endothelial cells transfected with the pcDNA33.1/CYP2J2 construct effectively formed epoxygenase metabolites at a rate of $17.8 \pm 2.3$ pmol/minute/$10^7$ cells (FIG. 1, bottom panel).

Method of screening. The invention provides a method of screening for an anti-inflammatory compound or a compound that prevents cell death from hypoxia-reoxygenation. In the method, a compound suspected of being an anti-inflammatory compound or a compound that prevents cell death from hypoxia-reoxygenation is administered to a cell, and the cytochrome P450 epoxygenase activity of the cell is assayed and measured. The cytochrome P450 epoxygenase activity measured is compared to the cytochrome P450 epoxygenase activity of a cell to which the suspected anti-inflammatory compound has not been administered. An increased cytochrome P450 epoxygenase activity of the treated cell as compared with the cytochrome P450 epoxygenase activity of the untreated cell identifies the test compound as an anti-inflammatory compound or a compound that prevents cell death from hypoxia-reoxygenation.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

EXAMPLE 1

Cytochrome P450 Epoxygenase Gene Activity in Endothelial Cells

Using reverse transcription-polymerase chain reaction (RT-PCR) on human endothelial cell mRNA, we isolated a cytochrome P450 epoxygenase cDNA clone (SEQ ID NO:1) that is identical to the CYP2J2 epoxygenase previously cloned from human liver tissues (GeneBank/EMBL accession numbers AF144566 and 1J37143) (Wu et al., 271 J. Biol. Chem. 3460 (1996)). Using 15 different pairs of degenerate oligonucleotides corresponding to conserved regions of cytochrome P450 epoxygenases, we performed RT-PCR on mRNA obtained from cultured human endothelial cells. Only one pair of primers (sense: 5'-GCTGACTTTCTCAAAAGACG-3' (SEQ ID NO:3); antisense: 5'-CTCTGCACCTCATGGATGAC-3' (SEQ ID NO:4), annealing/elongation temp: 51° C./72° C., 35 cycles) yielded a single band corresponding to a cDNA size of ~1 kb which was identical to the gene encoding CYP2J2 protein (SEQ ID NO:2), which is expressed in human cardiac tissues (Wu et al., 271 J. Biol. Chem. 3460 (1996)).

To study the formation of EETs by CYP2J2 in endothelial cells, we measured EET synthesis from bovine endothelial cells transfected with CYP2J2 cDNA. Early passage bovine aortic endothelial cells were grown to 60–70% confluence and transfected with either pcDNA3.1 or pcDNA3.1/CYP2J2 using Fugene™ 6 reagent (Boehringer Mannheim Corp.) according to the manufacturer's instructions. Using this method, the transfection efficiency was 10–20%. Forty-eight hours post-transfection, cells were washed twice with phosphate-buffered saline and incubated with freshly purified [$^3$H]arachidonic acid (185 Ci/mmol, 4–5 $\mu$Ci/175 mm$^2$ flask) and unlabeled arachidonic acid (10 $\mu$M) was added before addition of arachidonic acid. At various time points, the media and cells were removed and extracted with diethyl ether. The combined organic phases were dried under a nitrogen stream, resolved by reverse-phase high performance liquid chromatography (HPLC) and quantified by liquid scintillation as described by Wu et al., 271 J. Biol.

Chem. 3460 (1996). Products were identified by comparing their HPLC properties with those of authentic EET, dihydroxyeicosatrienoic acid (EHET), hydroxyeicosatetraenoic acid (HETE) and prostaglandin standards.

We observed radioactive peaks which co-migrated with authentic prostaglandins (3–7 min), DHETs (13–16 min). HETEs (17–22 min) and EETs (24–27 min) (FIG. 1, upper panel). The epoxygenase metabolites (the EETs and their stable hydration products, the DHETs) accounted for approximately half of the total reaction products and were formed at a rate of 7.7±2.1 pmol/minute/$10^7$ cells (n=3). This metabolic profile is comparable to that reported for bovine coronary artery endothelial cells (Rosolowsky et al., 1299 Biochim. Biophys. Acta. 267 (1996)) and is consistent with the ability of endothelial cells to rapidly hydrate EET to DHETs (VanRollins et al., 34 J. Lipid Res. 1931 (1993)). Endothelial cells transfected with the pcDNA33.1/CYP2J2 construct formed epoxygenase metabolites at a rate of 17.8±2.3 pmol/minute/$10^7$ cells (n=5, p<0.05 vs. pcDNA3.1 transfected cells) (FIG. 1, bottom panel). In the presence of the cytochrome P450 epoxygenase inhibitor, SKP525A (100 μM), the formation of epoxygenase metabolites by CYP2J2 transfected cells was inhibited by >80%.

EXAMPLE 2

Cytochrome P450 Epoxygenase CYP2J2 is Localized to the Human Coronary Artery

To determine whether CYP2J2 is localized to the human coronary artery, we stained formalin-fixed parafin-embedded human coronary artery tissue sections with a specific anti-CYP2J2 antibody. For immunohistochemistry, tissues were fixed in 10% neutral buffered formalin, processed, and embedded in paraffin. An affinity purified rabbit polyclonal antiserum to CYP2J2 (1:200 dilution) was used to detect CYP2J2 on serial sections (5–6 mm) of human heart, by the procedure of Wu et al., 271 J. Biol. Chem. 3460 (1996). The specificity of the CYP2J2 antibody was demonstrated by: (a) immunoblots of microsomal and S9 fractions prepared from various human tissues, in which the anti-CYP2J2 IgG produced a single band at 56 kDa corresponding to endogenous CYP2J2 protein; (b) the finding that anti-CYP2J2 IgG strongly reacted with recombinant CYP2J2 but not with other human cytochrome P450 isoforms such as the CYP1A, CYP2A, CYP2B, CYP2C, CYP2D and CYP2E subfamilies; and (c) there were no cross-reactive bands produced with the recombinant CYP4A isoforms CYP4A1, CYP4A2, CYP4A3, CYP4A8 and CYP4A11.

CYP2J2 immunoreactivity was abundant in the endothelium of both large and small coronary arteries. Staining was also present albeit much less intense, in vascular smooth muscle cells, whereas surrounding connective tissue stained relatively poorly.

EXAMPLE 3

Epoxyeicosatrienoic Acids Inhibit Upregulation of Adhesion Molecule Expression

To determine the biological effects of EETs, we treated tumor necrosis factor alpha (TNF-α)-stimulated human endothelial cells with physiological relevant concentrations (1–100 nM) of [5,6]-EET, [8,9]-EET, [11,12]-EET, [14,15]-EET, [11,12]-DHET.

Figure 2:
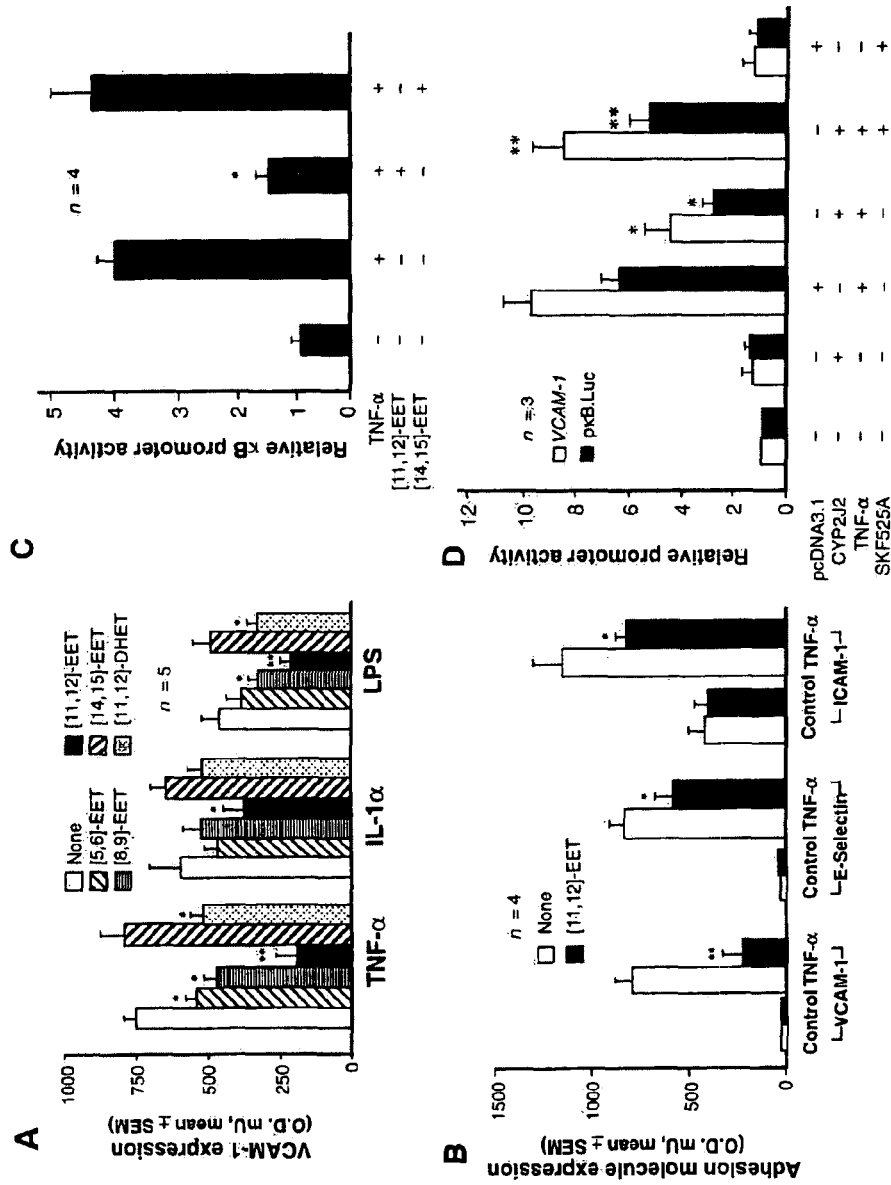
FIG. 2 is a set of bar graphs of cell-surface enzyme immunoassays.

Maximal 75% inhibition of TNF-α-induced vascular cell adhesion molecule-1 (VCAM-1) expression was achieved with [11,12]-EET, followed by [8,9]-EET, [5,6]-EET, and [11,12]-DHET (FIG. 2A). Unexpectedly, [14,15]-EET did not inhibit TNF-α-induced VCAM-1 expression indicating differential bioactivity of specific EET regioisomers. [11, 12]-EET also inhibited VCAM-1 expression in response to other inflammatory mediators such as interleukin (IL)-1α and bacterial lipopolysaccharide (LPS) (FIG. 2A), and it inhibited the expression of other adhesion molecules such as ICAM-1 and E-selectin suggesting a ventral mechanism its effect (FIG. 2, 3). In addition, two selective $K_{ca}$ channel blockers, iberiotoxin (100 nM) and charybodotoxin (100 nM) did not block the inhibitory effect of [11,12]-EET on TNF-α-induced VCAM-1 expression, indicating that the mechanism is independent of EET's hyperpolarizing effects.

EXAMPLE 4

P450 Derived Eicosanoids Modulate NF-κB and IκB Kinase Activity

To localize cis-acting elements in the VCAM-1 promoter that might mediate the inhibitory effects of [11,12]-EET, we transiently transfected bovine aortic endothelial cells with a −755 bp VCAM-1 promoter construct (DeCaterina et al., 96 J. Clin. Invest. 60 (1995)). Stimulation with TNF-α induced a 13-fold increase in relative VCAM-1 promoter activity that was abolished by cotreatment with [11,12]-EET. Similar inhibitory effect was observed with [11,12]-EET using a 98 bp VCAM-1 promoter construct containing the tandem κB cis-acting elements. To confirm that the tandem κB sites in the VCAM-1 promoter are repressed by [11,12]-EET we subcloned them into a heterologous promoter construct containing the SV40 enhancer linked to the luciferase reporter gene (pκB.Luc). Stimulation of transfected endothelial cells with TNF-α induced a 6-fold increase in pκB.Luc promoter activity that was abolished by co-treatment with [11,12]-EET, but not [14,15]-EET (FIG. 2C). To determine whether our CYP2J2 cDNA clone can functionally inhibit TNF-α induced VCAM-1 gene transcription, we overexpressed CYP2J2 in bovine aortic endothelial cells co-transfected with plasmid reporter gene constructs containing −755 bp VCAM-1 promoter or pκB.Luc. Compared to transfection with the empty pcDNA3.1 vector, overexpression of CYP2J2 decreased TNF-induced VCAM-1 and pκB.Luc promoter activity by 70–80% which were reversed in the presence of SKF525A (FIG. 2C). Neither transfection with CYP2J2 cDNA alone nor treatment with SKF525A alone affected basal promoter activity. These findings suggest that CYP2J2-derived eicosanoids repress VCAM-1 gene transcription, in part, by inhibiting κB cis-acting elements.

Since NF-κB activation involves the nuclear translocation of NF-κB subunits such as RelA, we assess the inhibitory effect of [11,12]-EET on the cellular localization of RelA unstimulated endothelial cells, RelA is predominantly localized to the cytoplasm, whereas cells stimulated with TNF-α showed an intense nuclear accumulation of RelA. Co-treatment with [11,12]-EET prevented the nuclear accumulation of RelA. Since the nuclear translocation of RelA requires the degradation of its endogenous cytoplasmic inhibitor, inhibitor kappa B (IκB-α), we followed the fate of IκB-α after TNF-α stimulation in the presence or absence of [11,12]-EET. Stimulation of human endothelial cells with TNF-α caused a rapid and almost complete disappearance of IκB-α which was prevented by co-treatment with [11,12]-EET, but not [14,15]-EET.

A set of gel shift assays was performed. One set of assays showed the fate Of IκB-α after treatment with TNF-α (10 ng/ml, 15 min) in the presence or absence of [11,12]-EET (100 nM) or [14,15]-EET (100 nM). Another set of assays showed IKK activity in unstimulated endothelial cells and endothelial cells stimulated with TNF-α (10 ng/ml, 15 min) in the presence and absence of [11,12]-EET (100 nM), [5,6]-EET (100 nM), or [8,9]-EET (100 nM). In some assays, [11,12]-EET (100 nM) was also added directly to the IKK assay (in vitro). As a control for nonspecific phosphorylation, the assay was performed without the addition of immunoprecipitated IKK (no enzyme) or in the presence of a IκB-α mutant (ΔSer 32, Ser 36→Thr) as substrate. The assay was performed three times with similar results.

Phosphorylation of IκB-α is regulated by IκB kinase (IKK) which specifically phosphorylates IκB-α at a serine residues 32 and 36 and targets IκB-α for subsequent degradation by 26S proteasomes (Palombella et al., 78 Cell 773 (1994). Inhibition of the specific 26S proteasome inhibitor, MG132, prevented the degradation of IκB-α following TNF-α stimulation. Using purified GST-1κB-α fusion protein as substrate, we found minimal basal IκB-α activity in unstimulated human endothelial cells Stimulation with TNF-α caused an increase in IKK activity which was inhibited by >90% In the presence of [11,12]-EET, and to a lesser extent in the presence of [5,6]-EET or [8,9]-EET. Specificity of IKB was determined by the complete absence of phosphorylation when the mutated IκB-α substrate, GST-1κB-α (Δ32,36: S→T) which cannot be phosphorylated at serine residues 32 and 36, was substituted for wild-type GST-IκB-α.

EXAMPLE 5

Epoxyeicosatrienoic Acids Prevent Leukocyte Adhesion to the Vascular Wall In Vivo To determine the functional relevance of EETs in vascular inflammation, we tested [11,12]-EET and its regioisomer [14,15]-EET in a recently developed in vivo model of TNF-α-induced VCAM-1 -mediated mononuclear cell adhesion in the murine carotid artery. Mononuclear cell adhesion to isolated-perfused mouse carotid arteries was investigated as described (Ramos et al., 84 Circ. Res. 1237 (1999) with some modifications. Briefly, C57BL/6 mice (Hilltop, Scottsdale, Pa.) mice were anesthetized with ketamine and xylazine, the right common carotid artery was cannulated with a PE10 perfusion catheter and the tip was advanced past the right subclavian artery into the brachiocephalic trunk. This is important, because EETs have a short half-life in vitro. Through this catheter, [11,12]-EET, [14,15]-EET, or vehicle was infused at a flow rate of 5 μl/min for a dose of 100 ng/kg/min for the remainder of the experiment (reference for dose). After 30 minutes, the mice were treated with an intraperitoneal injection of murine recombinant TNF-α (R&D Systems, Minneapolis, Minn.); 10 μg/kg in a volume of 200 μl PBS). Five hours later, the left common carotid artery was ligated and cannulated with a PE10 catheter in cranial direction. The carotid artery was perfused with heparinized MOPS-buffered physiological salt solution. The external and internal carotid branches were ligated with sutures and perforated by small punctures at the ends to produce similar outflow. The vessel was cut distal to each suture point and transferred to an intravital microscope stage, and was perfused with a suspension of mononuclear cells (U937 labeled with calcein AM) at a wall shear stress of about 3 dyn/cm$^3$.

Cell rolling and adhesion were recorded on videotape using stroboscopic epifluoresence illumination with an introvital microscope (objective Zeiss 20×, 0.5 numerical aperture). In mice receiving TNF-α only, the isolated vessels were also perfused with mAb MK-2 (40 μg/ml for 20 min) to block the function of VCAM-1. In separate experiments, VCAM-1 expression was measured in paraffin-sections (5 μm thick) of carotid arteries harvested from mice treated in the same way. Before staining, slides were incubated with avidin-biotin blocking reagent containing 5% rabbit serum (Vector Laboratories) to reduce background staining. Slides were incubated with primary antibody (polyclonal goat anti-mouse VCAM-1, Santa Cruz Biotechnology, Inc. Santa Cruz, Calif., 5 μg/ml) overnight at 4° C. in a humidified chamber followed by biotin-conjugated horse anti-goat (Vector Laboratories, Inc. Burlingame, Calif.), 0.03% hydrogen perozide in methanol, ABC complex (Vector Laboratories), and final development using 3,3'-diaminobenzidine (DAB) as substrate (Vector Laboratories). All antibody and ABC complex incubations were performed in the presence of 5% rabbit serum. Slides were counterstained with hematoxylin and eosin, washed in ethanol followed by xylene, and mounted. Slides were examined using a light microscope (Zeiss X100/1.4 oil immersion objective) (see, Ramos et al., 84 Circ. Res. 1237 (1999)).

Figure 3:
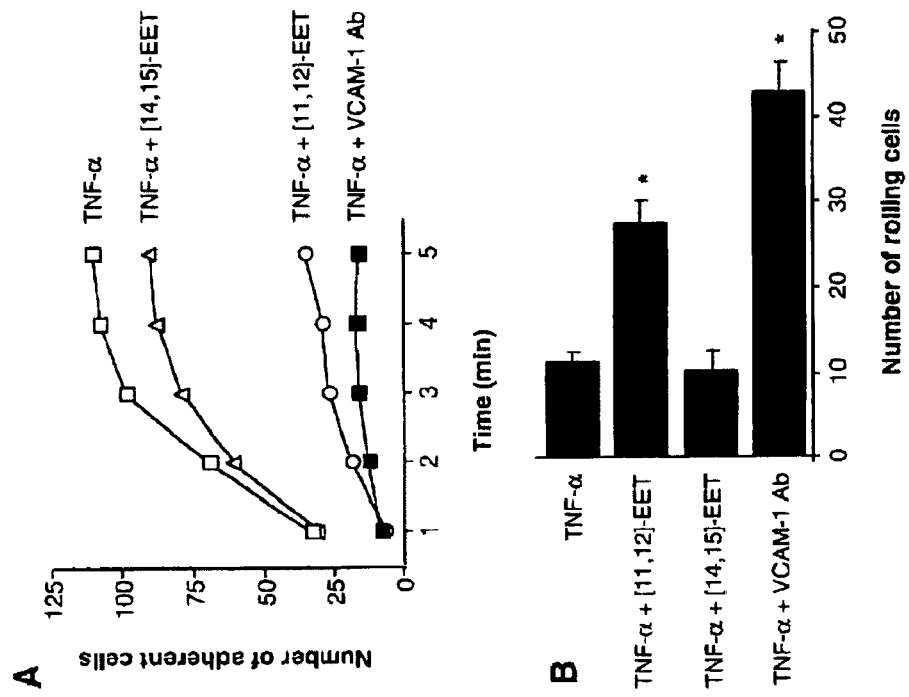
FIG. 3A is a graph showing the expression of VCAM-1 in the murine carotid artery at 5 hours after treatment with intraperitaneal injection of TNF-α (10 µg/kg) alone or in combination with continuous intra-arterial infusion of [11,12]-EET (100 ng/kg/min).
FIG. 3B is a bar graph showing the effect of [11,12]-EET on TNF-α induced mononuclear cell adhesion in the murine carotid artery. The mononuclear cells (U937) were perfused through the carotid artery at a wall shear stress of 3 dyn/cm$^2$. Intra-arterial infusion of vehicle (saline) or [14,15]-EET (100 ng/kg/min) had no effect. In vehicle-treated mice, most of the cell adhesion was blocked by mAb directed against VCAM-1 (MK2) (Miyake et al, 114 J. Cell Biol. 557 (1991)). All experiments except the [14,15]-EET infusion were performed in duplicate.

Under baseline conditions, mononuclear cells neither roll along nor adhere to the arterial endothelium. However, alter treatment with an intraperitoncal injection of TNF-αfor five hours, adhesion molecules including VCAM-1 and P-selectin are expressed on the endothelium, and mononuclear cells roll and adhere (Rarmos et al., 84 Circ. Res. 1237 (1999). In this model, cell rolling is dependent on endothelial P-selectin interacting with its ligand PSGL-1 on the mononuclear cells, and adhesion is dependent on endothelial VCAM-1 interacting with αβ integrin on the mononuclear cells. Intra-arterial infusion of [11,12]-EET, but not [14,15]-EET, decreased VCAM-1 expression and inhibited mononuclear cell adhesion to the vessel wall (FIG. 3). The mononuclear cell adhesion was blocked by a monoclonal antibody to VCAM-1 (Miyake et al, 114 J. Cell Biol. 557 (1991)). These findings, therefore, suggest an important anti-inflammatory property of EETs that is independent of their membrane hyperpolarizing or vasodilatory effect. Further studies may shed some light on the clinical importance of these epoxygenase-derived eicosanoids in attenuating vascular inflammation.

EXAMPLE 6

Episulfide and Sulfonamide EET Derivatives Inhibit VCAM-1 Expression

Figure 4:
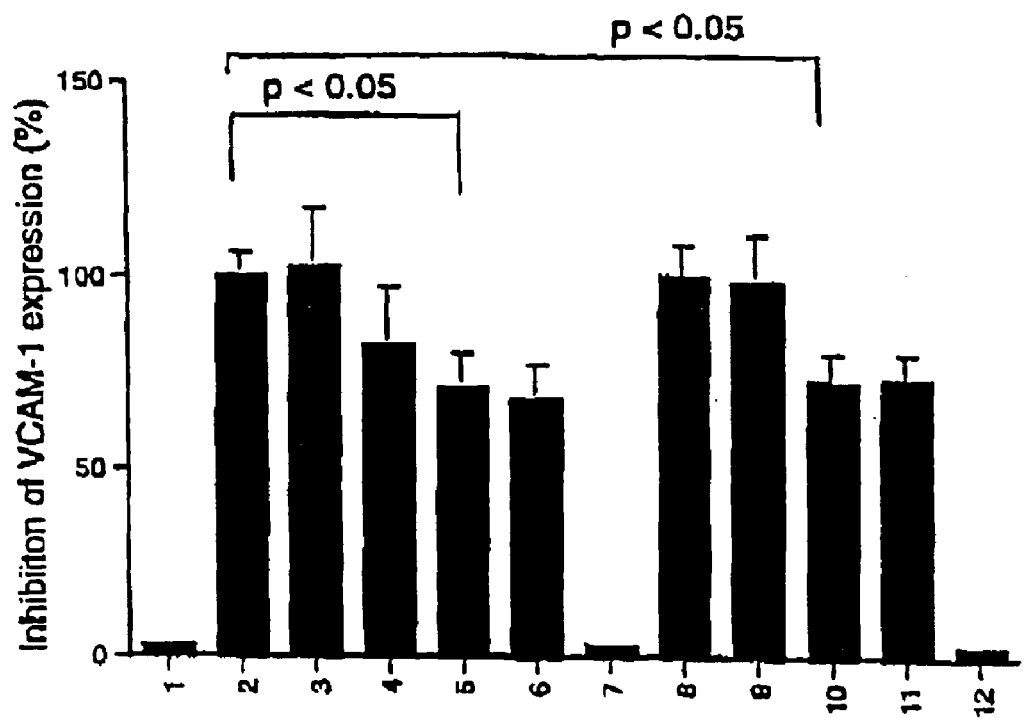
FIG. 4 is a bar graph showing two EET analogs, an episulfide derivative and a sulfonamide derivative, to demonstrate that both are active in inhibiting VCAM-1 expression.
Figure 11:
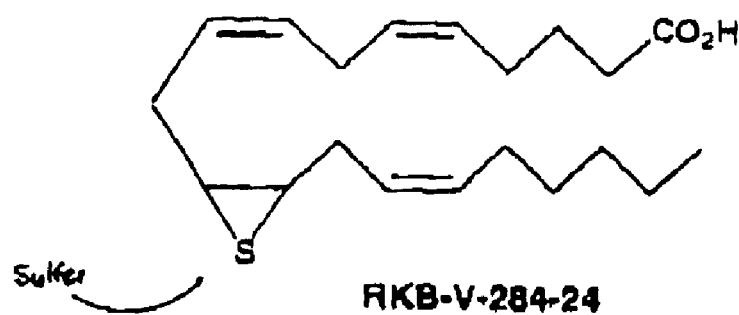
FIG. 11 is a pictorial representation of two EET analogs that are active in inhibiting VCAM-1 expression, RKB and KMR.
Figure 11:
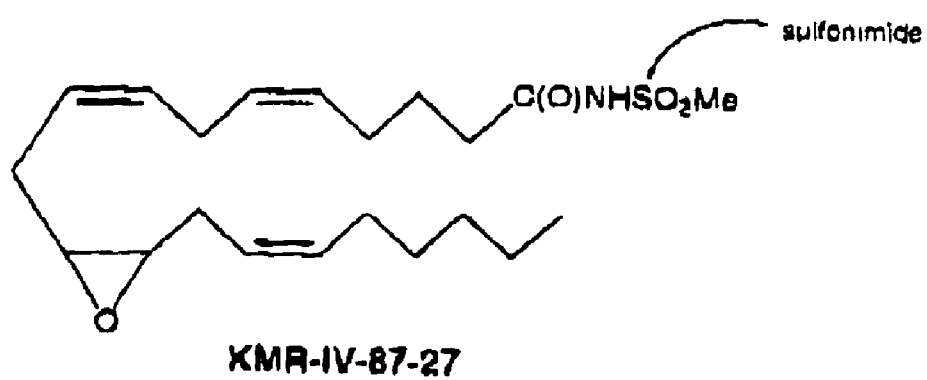

FIG. 4 is a bar graph showing that two EET analogs, an episulfide derivative and a sulfonamide derivative, to demonstrate that both derivatives are active in inhibiting VCAM-1 expression. The derivatives were designated RKB and KMR (see, FIG. 11). Methods were as described in EXAMPLE 3, above.

EXAMPLE 7

Overexpression of Cytochrome P450 CYP2J2 Protects Against Hypoxia-reoxygenation Injury in Cultured Bovine Aortic Endothelial Cells This EXAMPLE was designed to examine the role of CYP2J2 in hypoxia-reoxygenation (HR)-induced injury in cultured bovine aortic endothelial cells (BAECs). Early passage BAECs were exposed to 24 hr hypoxia followed by 4 hr reoxygenation. Hypoxia-reoxygenation resulted in cell injury, as indicated by significant increases in lactate dehydrogenase (LDH) release and trypan blue stained cells (p<0.01), and a decrease in CYP2J2 protein expression. Transfection of BAECs with a pcDNA3.1 vector containing the CYP2J2 cDNA resulted in increased CYP2J2 expression/epoxygenase activity, compared to control cells transfected with the irrelevant green fluorescent protein (GFP) cDNA. Hypoxia-reoxygenation induced significant injury in GFP-transfected BAECs, as indicated by increases in lactate dehydrogenase release and trypan blue stained cells (p<0.01); however, the hypoxia-reoxygenation-induced injury was markedly attenuated in CYP2J2-transfected cells (p<0.01). Hypoxia-reoxygenation increased cellular $F_2$-isoprostanes (p<0.05), and decreased eNOS expression and nitrite production (p<0.01) in GFP-transfected BAECs. CYP2J2 transfection attenuated the hypoxia-reoxygenation-induced increase in $F_2$-isoprostanes (p<0.05) and tended to preserve eNOS expression (p=0.08) and nitrite production (p=0.20) after hypoxia-reoxygenation. Superoxide anion formation by CYP2J2-transfected BAECs was significantly lower than that by GFP-transfected BAECs (p<0.05). Treatment of BAECs with synthetic EETs and/or epoxide hydrolase inhibitors also showed protective effects against hypoxia-reoxygenation injury (p<0.05). This EXAMPLE shows (a) hypoxia-reoxygenation results in endothelial injury and decreased CYP2J2 expression; (b) maintenance of CYP2J2 expression protects against hypoxia-reoxygenation injury; and (c) the mechanism for the protective effects of CYP2J2 involves both EET-dependent and EET-independent pathways.

Introduction. EETs have been shown to inhibit cytokine-induced endothelial cell adhesion molecule expression by inhibiting nuclear factor kappa B (NF-κB) and increase endothelial capacitative calcium entry, but their role in the response of endothelial cells to hypoxia-reoxygenation (HR) injury is unknown.

Vascular endothelial cells play a central role in cardiovascular physiology and pathobiology. Endothelial cell dysfunction is an important early event in virtually all forms of ischemia-reperfusion injury (Liao et al., 44 Clin. Chem. 1799–1808 (1998), Dzau et al., 18(SupplIII) Hypertension. III115–III121 (1991), Tan et al., 17 Eur. J. Vasc. Endovasc. Surg. 373–89 (1999), Biegelsen et al., 10 Coron. Artery Dis. 241–56 (1999), Lefer et al., 33 Annu. Rev. Pharmacol. Toxicol. 71–90 (1993)). The dysfunction appears to be triggered within 2.5 min of endothelial generation of oxygen free radicals such as superoxide anion (Lefer et al., 33 Annu. Rev. Pharmacol. Toxicol. 71–90 (1993)).

The relevance of reactive oxygen species generation and resultant lipid peroxidation in the pathogenesis of ischemia-reperfision injury has been extensively documented. Cellular $F_2$-isoprostane levels have been shown to be highly sensitive and specific markers for lipid peroxidation and also affect vascular tone (Mathews et al., 16 Free Radic. Biol. Med. 763–70 (1994), Morrow et al., 87 Proc. Natl. Acad. Sci. USA 9383–9387 (1990)). These eicosanoids are formed in vivo in humans via a non-enzymatic mechanism involving free radical-catalyzed peroxidation of arachidonic acid and have been proposed to participate as pathophysiological mediators in oxidant injury (Morrow et al., 87 Proc. Natl. Acad. Sci. USA 9383–9387 (1990)). Mathews et al. reported that a significant 60–250% increase in plasma $F_2$-isoprostane levels was observed during hepatic reperfusion following ischemia (Mathews et al., 16 Free Radic. Biol. Med. 763–70 (1994)). Reilly and co-workers also reported the evidence for increased oxidant stress during coronary artery reperfusion in humans, i.e., increased formation of the isoprostanes $IPF_{2\alpha}$-I and 8-epi-prostaglandin $F_{2\alpha}$ in acute coronary angioplasty (Reilly et al., 96 Circulation. 3314–3320 (1997)).

Since CYP2J P450s are abundant in heart tissue and localized to vascular endothelium, endothelial function is important in determining the degree of cellular injury following ischemia-reperfusion, and CYP2J products (the EETs) are cardioprotective, we determined that reduced endothelial CYP2J expression contributes to cellular dysfunction and is at least partly responsible for some of the pathophysiologic manifestations that follow ischemia-reperfusion. Furthermore, we postulated that the cellular injury could be abrogated either by maintaining the levels of CYP2J protein or by direct application of CYP2J-derived eicosanoids. Thus, this EXAMPLE was designed to determine whether maintenance of CYP2J2 levels in cultured bovine aortic endothelial cells (BAECs) affects hypoxia-reoxygenation-induced cell injury, and to understand the mechanisms involved.

Hypoxia-Reoxygenaiion Causes Cell Injury and Decreases Endothelial CYP2J Protein Expression. Early passage (third or fourth) bovine aortic endothelial cells (BAECs) were isolated and cultured in Dulbecco's Modified Eagle Medium (D-MEM) containing L-glutamine and 10% fetal bovine serum (Hyclone Laboratory, Logan, UT) under 95% air plus 5% carbon dioxide at 37° C. as described (Node et al., 285 Science 1276–1279 (1999), DeCaterina et al., 96 J. Clin. Invest. 60 (1995)).

Figure 5:
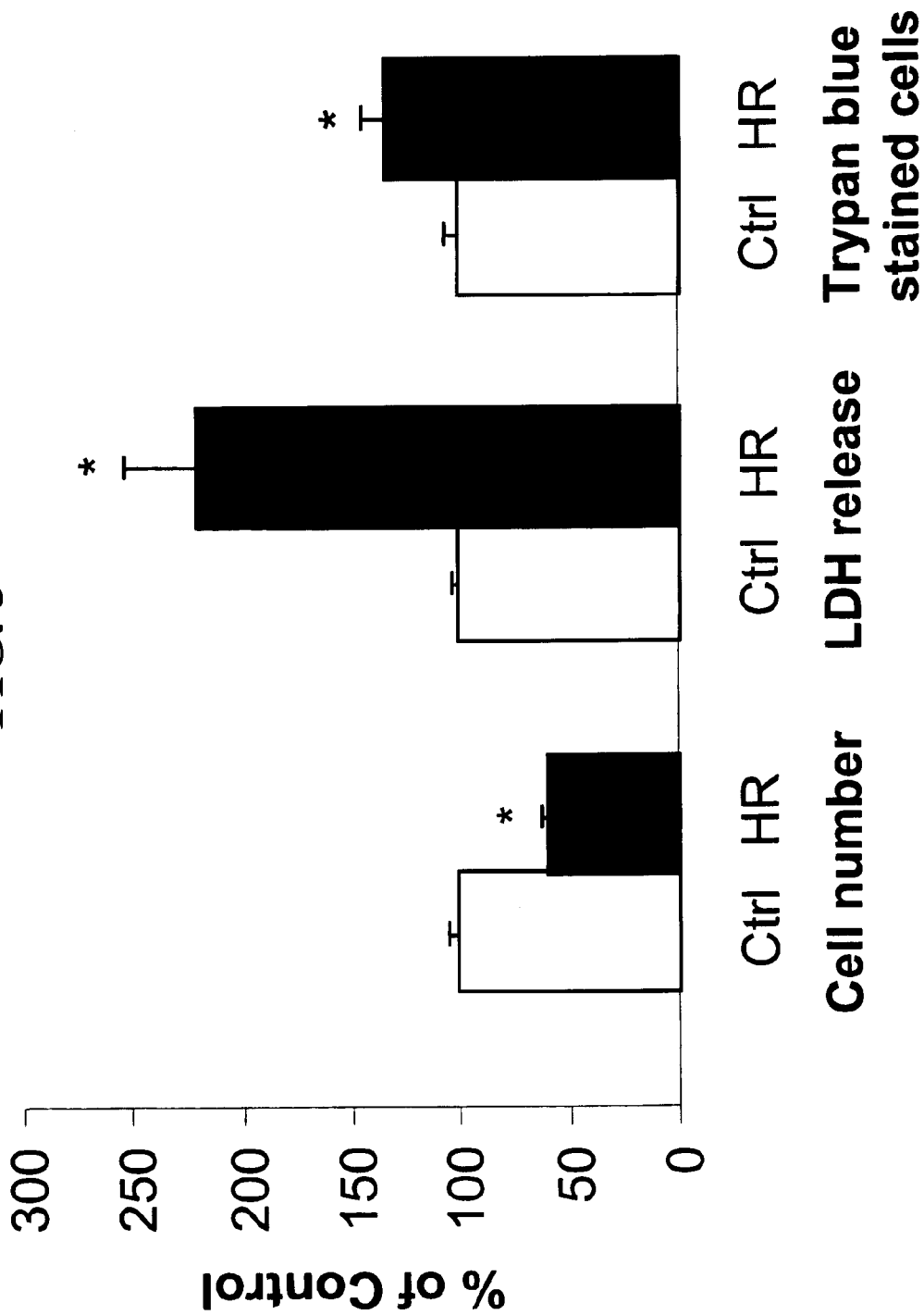
FIG. 5 shows the effect of hypoxia-reoxygenation (HR) on cell injury and CYP2J2 expression in cultured BAECs. BAECs were either maintained under nonnoxic conditions or exposed to hypoxia-reoxygenation. Cellular injury parameters and CYP2J2 expression were assessed. Exposure of BAECs to hypoxia-reoxygenation results in decreased cell number, increased lactate dehydrogenase (LDH) release and more trypan blue stained cells compared to BAECs maintained under normoxic conditions. Ctrl: control; HR: hypoxia-reoxygenation. *$p<0.01$ vs. control; N=12 in each group.

BAECs maintained under control (normoxic) conditions continued to grow and showed little evidence of cell injury. There were $1.56\pm0.12\times10^5$ cells/$cm^2$ surface area, lactate dehydrogenase release into the culture medium was $11.8\pm0.7$ mU/$10^5$ cells and $9.9\pm1.1\%$ of the cells stained with trypan blue. In contrast, BAECs exposed to 24 hours of hypoxia followed by 4 hours of reoxygenation exhibited a significant 40% decrease in cell number (p<0.01), lactate dehydrogenase release into the culture medium was increased by 120% (p<0.01), and there was a 34% increase in the number of trypan blue stained cells (p<0.01) (FIG. 5). These data are consistent with significant hypoxia-reoxygenation-induced endothelial cell injury and are in agreement with previous data on the effects of this stress in endothelial cells (Blanc et al., 19 Liver 42–49 (1999), Samarasinghe et al., 24 Hepatology. 1230–1237 (1996)).

Protein immunoblotting using a polyclonal antibody to recombinant human CYP2J2 that cross-reacts with CYP2J isoforms in rabbit, rat, and mouse (see below for methods) revealed the presence of an abundant 56 kDa protein band in control BAEC lysates. This protein, which has an electrophoretic mobility slightly lower than that of recombinant CYP2J2 (57 kDa) and CYP2J2 present in human tissues, likely represents the bovine orthologue of human CYP2J2. Interestingly, the expression of this CYP2J2 immunorcactive protein was markedly reduced in BAECs that were exposed to hypoxia-reoxygenation.

An immunoblot assay showed that exposure of BAECs to hypoxia-reoxygenation decreases CYP2J2 protein expression. The assay was performed with recombinant CYP2J2 as a positive control; BAECs maintained under normoxic conditions, as negative controls; and BAECs exposed to hypoxia-reoxygenation.

This decreased expression appears to be relatively selective for CYP2J2 in that the expression of angiotensin II type I receptor and ICAM-1 remain unchanged or increase following exposure of endothelial cells to hypoxia-reoxygenation.

Transfection of BAECs with pcDNA3.1/CYP2J2 and EET biosynthesis. The CYP2J2 cDNA (1.9 kb) or GFP cDNA (0.75 kb) were subcloned into the plasmid pcDNA3.1 (Invitrogen, Carlsbad, Calif.) at the EcoR I and Xho I sites. Restriction enzyme digestion and sequence analysis using the dRhodamine Terminator Cycle Sequencing Ready Reaction Kit (Perkin Elmer, Foster City, Calif.) and an ABI Model 377 Automated DNA Sequencer (Perkin Elmer) confirmed the identity of the resulting pcDNA3.1/GFP and pcDNA3.1/CYP2J2 plasmids. Plasmids were purified using the Qiagen Plasmid Purification Kit (Qiagen, Inc., Chatsworth, Calif.) according to the manufacturer's instructions. BAECs grown to ~50% confluency were transfected with either the pcDNA3.1 empty vector, pcDNA3.1/GFP or pcDNA3.1/CYP2J2 (0.1 $\mu$g DNA/cm$^2$) using FuGENE 6 transfection reagent (Roche Molecular Biochemicals, Indianapolis, Ind.) according to the manufacturer's transfection protocol (DNA:FuGENE 6=1 $\mu$g:3 $\mu$l). Forty-eight hours later, cells transfected with the pcDNA3.1/GFP vector were examined using a Zeiss Model LSM-410 inverted confocal laser scanning microscope (Zeiss, Thornwood, N.Y.) to determine transfection efficiency.

Forty-eight hours after transfection of BAECs with the pcDNA3.1/GFP construct, ~20% of the cells exhibited strong green fluorescence, indicating significant Green Fluorescent Protein (GFP) expression. Forty-eight hours after transfection of BAECs with pcDNA3.1/GFP, ~20% of cells exhibit strong green fluorescence.

Immunoblotting of lysates prepared from these C-FP-transfected cells with the anti-CYP2J2 IgG revealed expression of the constitutive 56 kDa bovine CYP2J2 orthologue, the abundance of which was unchanged compared to untransfected cells or to cells transfected with the empty pcDNA3.1 vector. Immunoblotting showed that CYP2J2 protein expression is increased in BAECs transfected with pcDNA3.1/CYP2J2. Lysates prepared from CYP2J2-transfected BAECs as contols; and also prepared from GFP-transfected BAECs.

Immunoblotting for CYP2J protein was performed as follows: Forty-eight hours after transfection of BAECs with either pcDNA3.1/GFP or pcDNA3.1/CYP2J2, cells were collected by treatment with tiypsin and either lysed in 1% SDS, 0.1% Triton-X100, 10 mmol/L Tris-HCl, pH 7.4 or used to prepare microsomal and mitochondrial fractions by differential centrifugation at 4° C. as described (Wu el al., 272 J. Biol. Chem 12551 (1997), Isaya et al., 8 Mol. Cell. Biol. 5150–5158 (1988)). Proteins were separated on SDS-12% (w/v) Tris-Glycine precast gels (NOVEX, San Diego, Calif.) and the resolved proteins were transferred electrophoretically onto nitrocellulose membranes. The membranes were then immunoblotted with affinity purified rabbit polyclonal anti-human CYP2J2 IgG (1:2000 dilution), goat anti-rabbit IgG conjugated with horseradish peroxidase (Bio-Rad, Hercules, Calif.), and the ECL Western Blotting Detection System (Amersham, Arlington Heights, Ill.) as described (Wu et al., 271 J. Biol. Chem. 12551 (1996)). For some experiments, cells were exposed to hypoxia-reoxygenation prior to immunoblotting for CYP2J protein. The anti-CYP2J2 IgG cross-reacts with known CYP2J subfamily P450s in human, rabbit, rat, and mouse but does not recognize other P450 isoforms including members of the CYP1A, CYP2A, CYP2B, CYP2C, CYP2D, CYP2E and CYP4A subfamilies (Wu et al., 272 J. Biol. Chem 12551 (1997), Node et al., 285 Science 1276–1279 (1999)).

Figure 6:
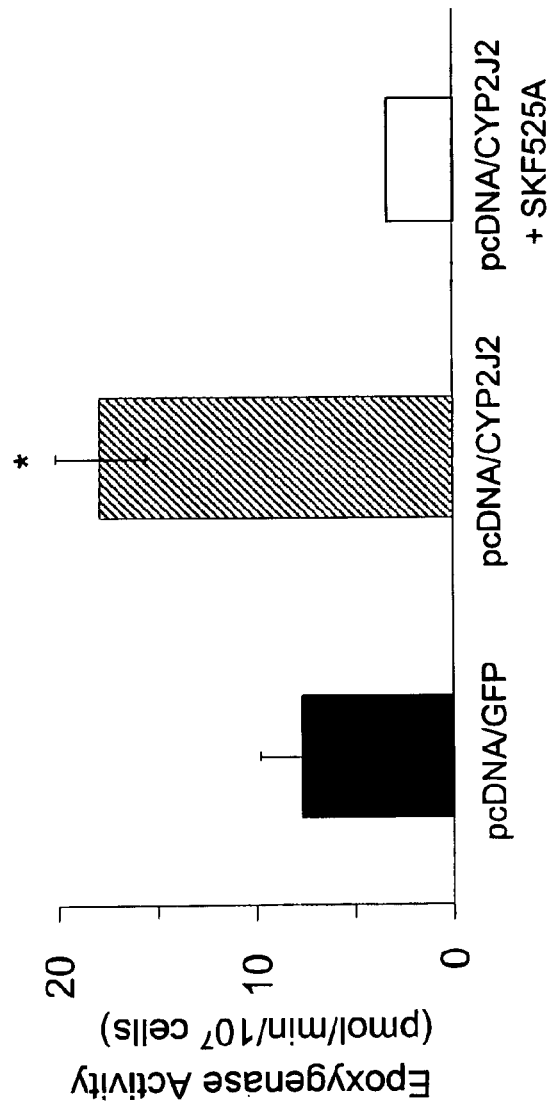
FIG. 6 shows the CYP2J2 expression and arachidonic acid epoxygenase activity in transfected BAECs. Cells were transfected with either pcDNA3.1/GFP or pcDNA3.1/CYP2J2. Forty-eight hours later, transfection efficiency was assessed by fluorescence microscopy, CYP2J2 expression was evaluated by immunoblotting and arachidonic acid epoxygenase activity was determined by HPLC. Arachidonic acid epoxygenase activity is increased in CYP2J2-transfected BAECs (N=4) compared to GFP-transfected cells (N=4) and CYP2J2-transfected cells treated with SKF-525A (N=2). *$p<0.05$ vs. GFP-transfected cells.

These control GFP-transfected cells metabolized radiolabeled arachidonic acid to epoxygenase metabolites (EETs and DHETs) at a rate of ~8 pmol/min/10$^7$ cells (FIG. 6).

Endothelial cell arachidonic acid metabolism was determined as follows: Forty-eight hours after transfection with either pcDNA3.1/GFP or pcDNA3.1/CYP2J2, BAECs were incubated with freshly purified [5, 6, 8, 9, 11, 12, 14, 15-$^3$H]arachidonic acid (185 Ci/mmol, 4–5 $\mu$Ci/175-mm$^2$ flask) in serurm-free culture medium at 37° C. for 30–120 min. In some experiments, the P450 inhibitor SKF-525A (100 $\mu$mol/L, final concentration) was added before the addition of arachidonic acid. The BAECs and culture medium were then collected and the reaction products extracted into ethyl ether, dried under a nitrogen stream, analyzed by reverse-phase HPLC, and quantified by on-line liquid scintillation using a Radiomatic Flo-One β detector (Radiomatic Instruments, Tampa, Fla.) as described (Wu et al., 271 J. Biol. Chem. 12551 (1996), Node et al., 285 Science 1276–1279 (1999)). Products were identified by comparing their reverse-phase HPLC properties with those of authentic EET, DHET, HETE, and prostaglandin standards, and by gas chromatography/mass spectrometry.

Transfection of endothelial cells with the pcDNA3.1 expression vector containing the CYP2J2 cDNA resulted in abundant expression of a 57 kDa CYP2J2 immunoreactive protein. This recombinant CYP2J2 protein was present in whole cell lysates and in both microsomal and mitochondrial subcellular fractions. The increase in CYP2J2 expression was accompanied by a significant increase in endothelial arachidonic acid epoxygenase activity ($p<0.05$) (FIG. 6). The increased epoxygenase activity was inhibited in the presence of the P450 inhibitor SKF-525A. Based on this data, we conclude that: (a) CYP2J2 is constitutively expressed in GFP-transfected BAECs; (b) these cells biosynthesize EETs from arachidonic acid; and (c) increased CYP2J2 expression is accompanied by increased epoxygenase activity.

Protective effect of CYP2J2 transfection on hypoxia-reoxygenation-induced injury in BAECs. In preliminary tests, we determined the effects of transfection alone on BAECs under normoxic conditions. Transfection of BAECs with either pcDNA3.1 empty vector, pcDNA3.1/GFP or pcDNA3.1/CYP2J2 resulted in 28–38% fewer cells, 20–33% increase in the number of trypan blue stained cells, 250–350% increase in cellular lactate dehydrogenase release, and 40–50% lower cellular eNOS expression, compared to untreated cells or cells treated with FuGENE 6 reagent alone (all $p<0.05$). There were no significant differences between GFP- and CYP2J2-transfected BAECs in any of these parameters under normoxic conditions. Sensitivity to hypoxia-reoxygenation-induced injury was also more pronounced in empty vector or GFP-transfected cells compared to cells treated with FuGENE 6 reagent alone, as indicated by a ~20% increase in the number of trypan blue stained cells and ~20% higher lactate dehydrogenase in the culture media ($p<0.05$).

Figure 7:
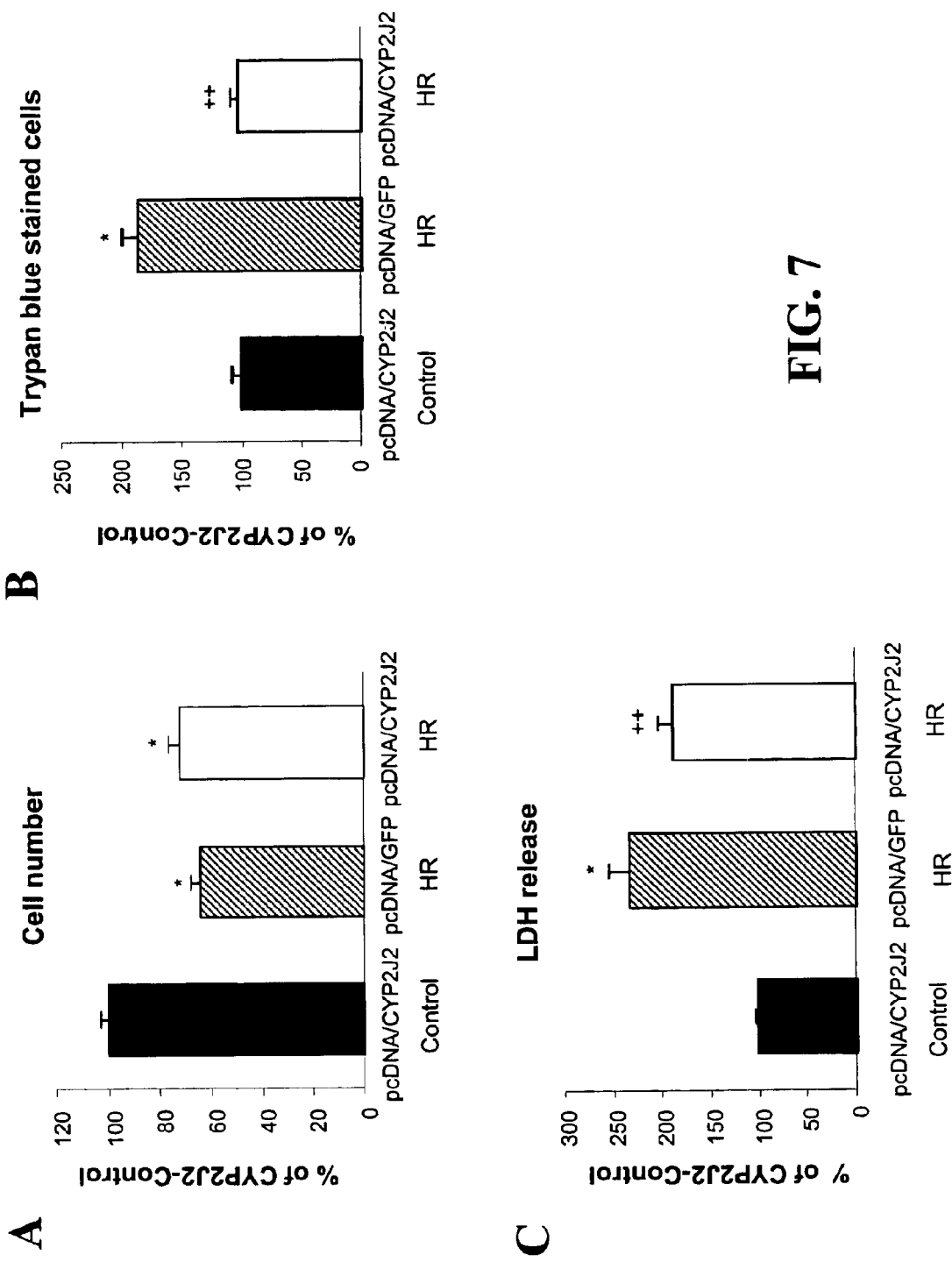
FIG. 7 shows the effect of CYP2J2 transfection on cell injury parameters and CYP2J2 protein expression in BAECs exposed to hypoxia-reoxygenation. Forty-eight hours after transfection of BAECs with either pcDNA3.1/GFP or pcDNA3.1/CYP2J2, cells were exposed to hypoxia-reoxygenation. Cell injury parameters and CYP2J2 expression were determined.

Compared to either GFP-transfected cells or CYP2J2-transfected cells maintained under normoxic conditions, GFP-transfected BAECs exposed to 24 hours of hypoxia followed by 4 hours of reoxygenation exhibited a 36% reduction in cell number, lactate dehydrogenase release into the culture medium was increased by 230%, and there was a 86% increase in the number of trypan blue stained cells (all $p<0.01$) (FIG. 7B). These data are consistent with significant hypoxia-reoxygenation-induced endothelial cell injury in GFP-transfected cells. Importantly, the hypoxia-reoxygenation-induced cell injury was markedly attenuated in CYP2J2-transfected BAECs. Thus, cell number was slightly increased ($p=0.154$), significantly less lactate dehydrogenase was released into the culture medium ($p<0.01$)

and there were significantly fewer trypan blue stained cells (p<0.01) in CYP2J2-transfected compared to GFP-transfected BAECs exposed to hypoxia-reoxygenation (FIG. 7B). Immunoblots confirmed that CYP2J2-transfected cells maintained higher levels of immunoreactive CYP2J2 protein than GFP-transfected cells after exposure to hypoxia-reoxygenation. CYP2J2 protein levels were increased in CYP2J2-transfected cells under both normoxic and hypoxia-reoxygenation conditions.

Together, these data demonstrate that maintenance of CYP2J2 protein levels is associated with reduced hypoxia-reoxygenation-induced cellular injury. CYP2J2 and/or its products are protective in endothelial cells.

Effects of P450-derived arachidonic acid metabolites on hypoxia-reoxygenalion-induced injury in BAECs. BAECs, either untransfected, or 48 hours after transfection with pcDNA3.1/GFP or pcDNA3.1/CYP2J2, or 10 min after treatment with eicosanoids, epoxide hydrolase inhibitors or vehicle, were exposed to hypoxia (95% nitrogen plus 5% carbon dioxide) for 24 hours, followed by reoxygenation (95% air plus 5% carbon dioxide) for 4 hours using an environmental chamber within a 37° C. incubator. Cells maintained under continuous (28 hours) normoxic conditions served as controls. The hypoxia resulted in a significant decrease in oxygen tension in the culture medium to 30 mmHg.

EETs were prepared by total chemical synthesis as previously described (Corey el al., 102 J. Am. Chem. Soc. 1433–1435 (1980), Falck et al., 23 Tetrahedron Lett. 1755–1756 (1982)). DHETs were prepared by chemical hydration of EETs as described by Capdevila et al., 187 Methods Enzymol. 386–394 (1990). Synthetic EETs and DHETs were purified by reverse-phase HPLC prior to use. BAECs, grown to ~85% confluency, were treated with either synthetic [11,12]-EET, [11,12]-DHET, or [14,15]-EET in ethanol vehicle (1 $\mu$mol/L each, final concentration) for 10 min prior to exposure to hypoxia-reoxygenation. In parallel experiments, the specific soluble epoxide hydrolase inhibitor dicyclohcxylurea (DCU, Ki=30 nmol/L, 10 $\mu$mol/L final concentration) (Morisseau et al., 96 Proc. Natl. Acad. Sci. USA 8849–8854 (1999)) and the specific microsomal epoxide hydrolase inhibitor elaidamide in DMF vehicle (10 $\mu$mol/L final concentration) was added together with [11,12]-EET. Cells treated with vehicle alone served as controls.

After hypoxia-reoxygenation, the cell number was determined using a hemocytometer and the degree of cell injury was assessed by measuring lactate dehydrogenase release into the culture medium using the CytoTox 96 Non-Radioactive Cytotoxicity Assay Kit (Promega, Madison, Wis.) and by counting the number of trypan blue dye stained cells. Data are expressed as a percentage of values obtained from control cells maintained under normoxic conditions.

All data were obtained from 3–20 separate experiments and expressed as mean±SEM. Data were compared by analysis of variance (ANOVA) using SYSTAT software (SYSTAT Inc., Evanston, Ill.). When F values indicated that a significant difference was present, Fishers LSD test for multiple comparisons was used. Values were considered significantly different if P was <0.05.

Figure 8B:
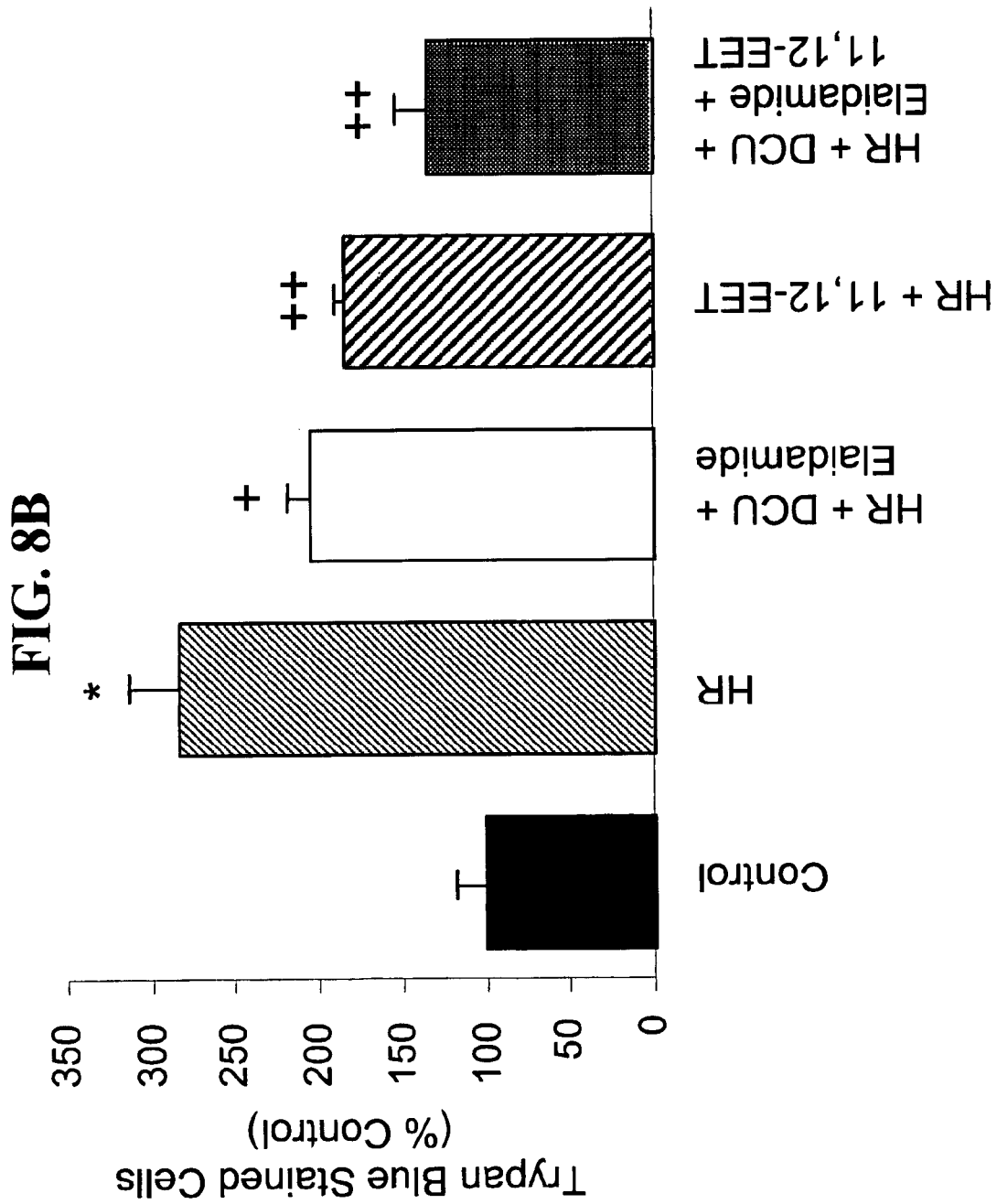
(FIG. 8B) Addition of epoxide hydrolase inhibitors DCU (10 µmol/L) and elaidamide (10 µmol/L) 30 min prior to hypoxia or 1 µmol/L [11,12]-EET 10 min prior to hypoxia significantly attenuates hypoxia-reoxygenation-induced cell injury in BAECs. The effects of [11,12]-EET and epoxide hydrolase inhibitors are additive. *$p<0.01$ vs. control; $^+p<0.05$ vs. hypoxia-reoxygenation; $^{++}p<0.01$ vs. hypoxia-reoxygenation; N=5 in each group.

The beneficial effects of CYP2J2 transfection are mediated, at least in part, by arachidonic acid metabolites. Thus, addition of 1 $\mu$mol/L [11,12]-EET to the culture medium 10 min prior to hypoxia significantly attenuates hypoxia-reoxygenation-induced cell death as measured by the number of trypan blue stained cells (p<0.05) (FIG. 8A and FIG. 8B). Other epoxygenase products such as [14,15]-EET and the [11,12]-DHET were also active in attenuating the effects of hypoxia-reoxygenation, albeit to a lesser extent than [11,12]-EET (FIG. 8A). Similarly, addition of the soluble epoxide hydrolase inhibitor dicyclohexylurea and the microsomal epoxide hydrolase inhibitor elaidamide (which decrease EET hydrolysis and prolong the half-life of endogenous EETs) also limits hypoxia-reoxygenation-induced endothelial cell injury (p<0.05) (FIG. 8B). The combination of [11,12]-EET and epoxide hydrolase inhibitors are additive (p<0.01).

Figure 9A:
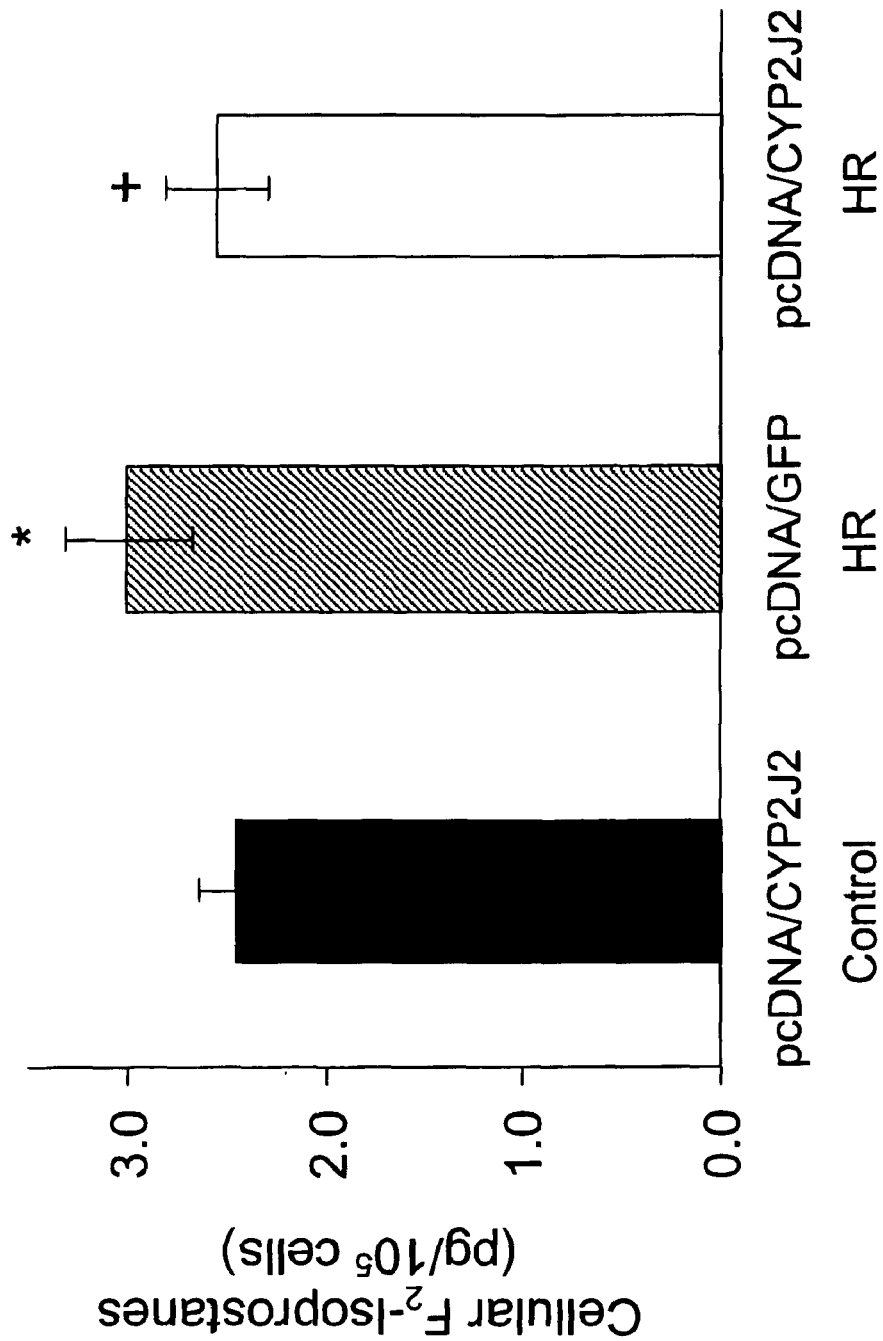
(FIG. 9A) Forty-eight hours after transfection of BAECs with either pcDNA3.1/GFP or pcDNA3.1/CYP2J2, cells were exposed to hypoxia-reoxygenation. Cellular F$_2$-isoprostanes were measured *$p<0.05$ vs. CYP2J2-transfected cells maintained under normoxic conditions; $^+p<0.05$ vs. GFP-transfected cells exposed to hypoxia-reoxygenation; N=5–6 in each group.

Reactive oxygen species generation, lipid peroxidation and CYP2J2-mediated protection in BAECs To examine whether some of the beneficial effects of CYP2J2 overexpression were mediated by influences on reactive oxygen species generation, we used established GC/MS methods to quantify 8-iso-PGF$_{2\alpha}$ in control BAECs and in cells exposed to hypoxia-reoxygenation. Compared to CYP2J2-transfected cells maintained under normoxic conditions, GFP-transfected BAECs exposed to 24 hours of hypoxia followed by 4 hours of reoxygenation had 20–25% higher levels of cellular F$_2$-isoprostanes (p<0.05) (FIG. 9A). Interestingly, transfection with the CYP2J2 containing vector significantly attenuated this increase (p<0.05) (FIG. 9A).

F$_2$-Isoprostane levels in BAECs were measured using a modification of the procedure described by Morrow & Roberts, 300 Methods Enzymol. 3–12 (1999). Briefly, cells were collected by treatment with trypsin and stored at −80° C. until analyzed. BHT was added to the freshly-thawed samples to inhibit oxidation during sample processing. The samples (4×10$^7$ cells) were incubated with KOH for 30 minutes at 40° C. The samples were then acidified to pH 3.0, 3 ng of a d$_4$ 8-iso-PGF$_{2\alpha}$ internal standard was added, and the precipitated protein was removed by centrifugation at 375×g. The F$_2$-isoprostanes in the supernatant were concentrated by passage over C$_{18}$ Sep-pak (Millipore, Marlborough, Mass.), followed by Silica Sep-pak (Millipore) columns. The eluant, containing a mixture of the d$_4$ internal standard and endogenous cellular F$_2$-isoprostanes, was dried under nitrogen and derivatized to the pentaflorobenzyl (PFB) ester using $\alpha$-bromo-2,3,4,5-pentafluorotoluene according to the protocol of Schweer et al., 32 J. Mass Spectrom. 1362–1370 (1997). The PFB-derivatized isoprostanes were purified by TLC, and the bands were collected based on comparison of their R$_f$ values to those of authentic standards. The derivatized isoprostanes were eluted from the silica gel with the TLC developing solvent, and further derivatized with bis(trimethylsilyl) trifluoroacetamide as described by Morrow & Roberts, 300 Methods Enzymol. 3–12 (1999). Quantitation was done by GC/NCI/MS on a 25m Supelco DB 5 column (Supelco, Bellefonte, Pa.). The ratio of the (M-181) peak height of the d$_0$ 8-iso-PGF$_{2\alpha}$ from the sample was compared to that of the d$_4$ 8-iso-PGF2$\alpha$ internal standard. All injections were done in duplicate.

Figure 9B:
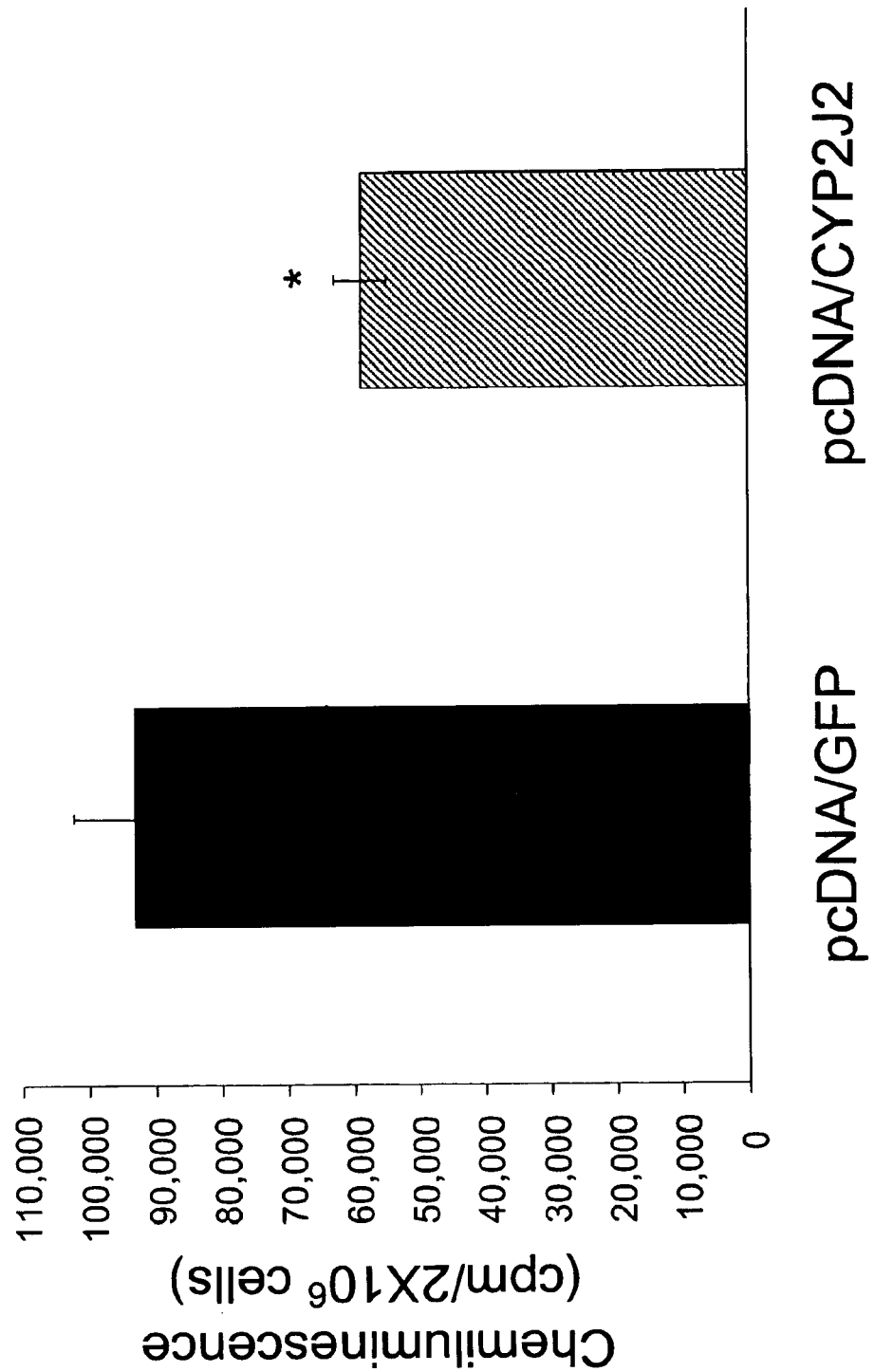
(FIG. 9B) Forty-eight hours after transfection of BAECs with either pcDNA3.1/GFP or pcDNA3.1/CYP2J2, superoxide anion formation was assessed by chemiluminescence of lucigenin. *$p<0.05$ vs. GFP-transfected cells; N=3 in each group.

Furthermore, the rate of superoxide anion formation, as determined by chemiluminescence of lucigenin, was significantly lower in CYP2J2-transfected cells compared to GFP-transfected cells (p<0.05) (FIG. 9B). The rate of superoxide anion generation by BAECs was determined as follows: Forty-eight hours after transfection with either pcDNA3.1/GFP or pcDNA3.1/CYP2J2, BAECs were detached by treatment with trypsin and resuspended in culture medium containing 10% FBS. Special care was taken to avoid unnecessary manipulation of the BAECs. The rate of superoxide anion formation in vitro was determined by chemiluminescence of lucigenin (bis-N-methylacridinium nitrate) as described by Yang et al., 274 Am. J. Physiol. H1955–H1961

(1998)). Briefly, culture medium (10% of FBS added) containing 0.25 mmol/L lucigenin (pH 7.4) was prepared as an assay solution. One milliliter of this assay solution was placed in a plastic scintillation vial., and then $2\times10^6$ BAECs were gently placed in the assay solution. The chemiluminescence of lucigenin was then detected with the use of a scintillation counter (LS 6500, Beckman Instruments, Fullerton, Calif.) in out-of-coincidence mode with a single active photomultiplier tube every 5 min. The chemical specificity of this light-yielding reaction for superoxide anion has been reported previously (Yang et al., 274 Am. J. Physiol. H1955–H1961 (1998)). The specificity of this assay with xanthine (100–400 nmol/L) and xanthine oxidase (0.002 U) was determined, and the chemiluminescence was totally blocked by superoxide dismutase (Gyllenhammar et al., 97 J. Immunol. Methods. 209–213 (1987)).

Together, these results show that the mechanism for the protective effects of CYP2J2 in endothelial cells also involves an EET-independent, oxidant mediated pathway.

Nitric oxide pathway, AT1 Receptor, and CYP2J2-mediatedprotection of BAECs. To determine if the nitric oxide pathway was involved in the protective effects of CYP2J2 transfection in BAECs, we examined constitutive eNOS expression and activity. BAECs collected after hypoxia-reoxygenation were lysed in 1% SDS, 0.1% Triton-X100, 10 mmol/L Tris-HCl (pH 7.4) and the total cellular lysate clarified by centrifugation at 10,000 rpm for 2 min. Proteins were separated on 12% Tris-Glycine gels (NOVEX), transferred to nitrocellulose, and then immunoblotted with rabbit polyclonal anti-AT1 receptor IgG (Santa Cruz Biotechnology, Inc., Santa Cruz, Calif.), mouse monoclonal anti-eNOS IgG (BIOMOL Research Laboratories, Inc., Plymouth Meeting, Pa.), or rabbit polyclonal anti-iNOS IgG (BIOMOL Research Laboratories, Inc.) according to the manufacturer's instructions. Corresponding anti-rabbit IgG or anti-mouse IgG were used s as the secondary antibody and the blots were visualized with ECL Western Blotting Detection System (Amersham) (Li et al., 41 Cardiovasc. Res. 109–115 (1999)). Densitometry was performed on autoradiographs using a Microtek ScanMaker III scanning densitometer. Nitrite levels in the culture medium were determined using the Griess reagent system (Promega) (Green et al., 126 Anal. Biochem. 131–138 (1982)).

Figure 10A:
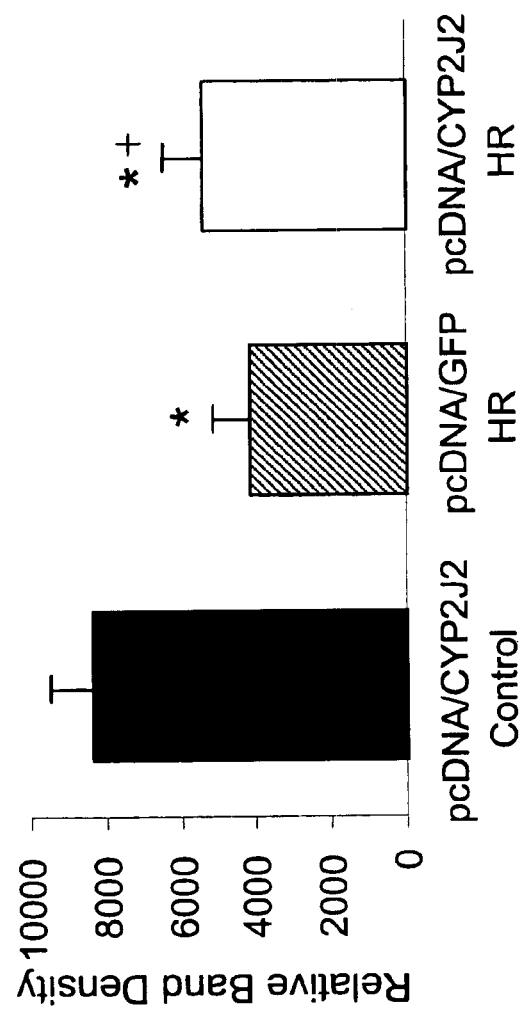
(FIG. 10A) Immunoblotting shows reduced eNOS expression in GFP-transfected BAECs exposed to hypoxia-reoxygenation. There is a trend toward higher expression of eNOS in CYP2J2 transfected cells exposed to hypoxia-reoxygenation. $*p<0.01$ vs. CYP2J2 transfected cells maintained under nornoxic conditions; $^+p=0.08$ vs. GFP-transfected cells exposed to hypoxia-reoxygenation; N=3 in each group.
Figure 10B:
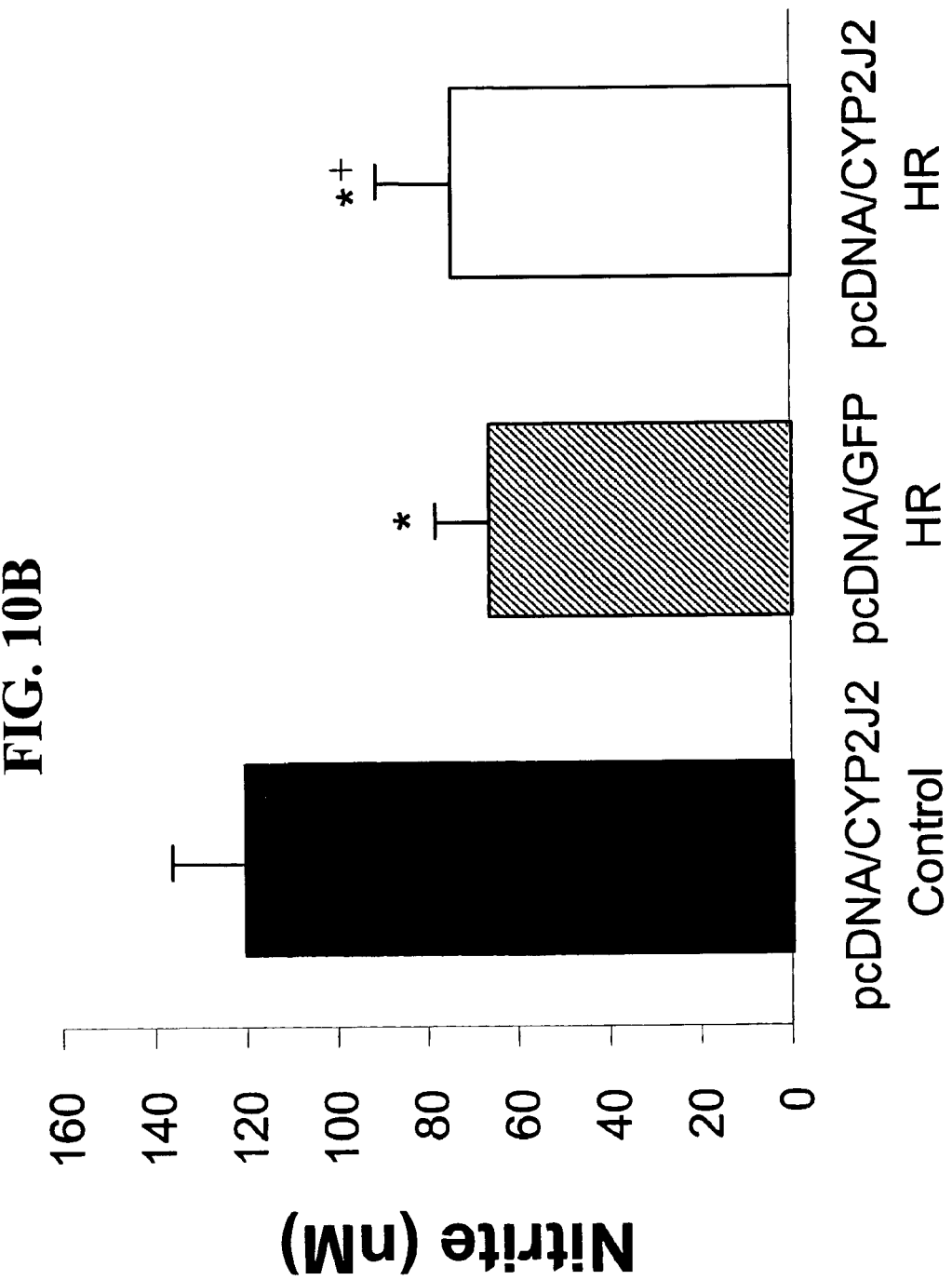
(FIG. 10B) Nitrite production is lower in GFP-transfected BAECs exposed to hypoxia-reoxygenation. There is a trend toward higher nitrite levels in CYP2J2-transfected cells exposed to hypoxia-reoxygenation. $*p<0.01$ vs. CYP2J2 transfected cells maintained under normoxic conditions; $^+p=0.20$ vs. GFP-transfected cells exposed to hypoxia-reoxygenation; N=3 in each group.
Figure 10C:
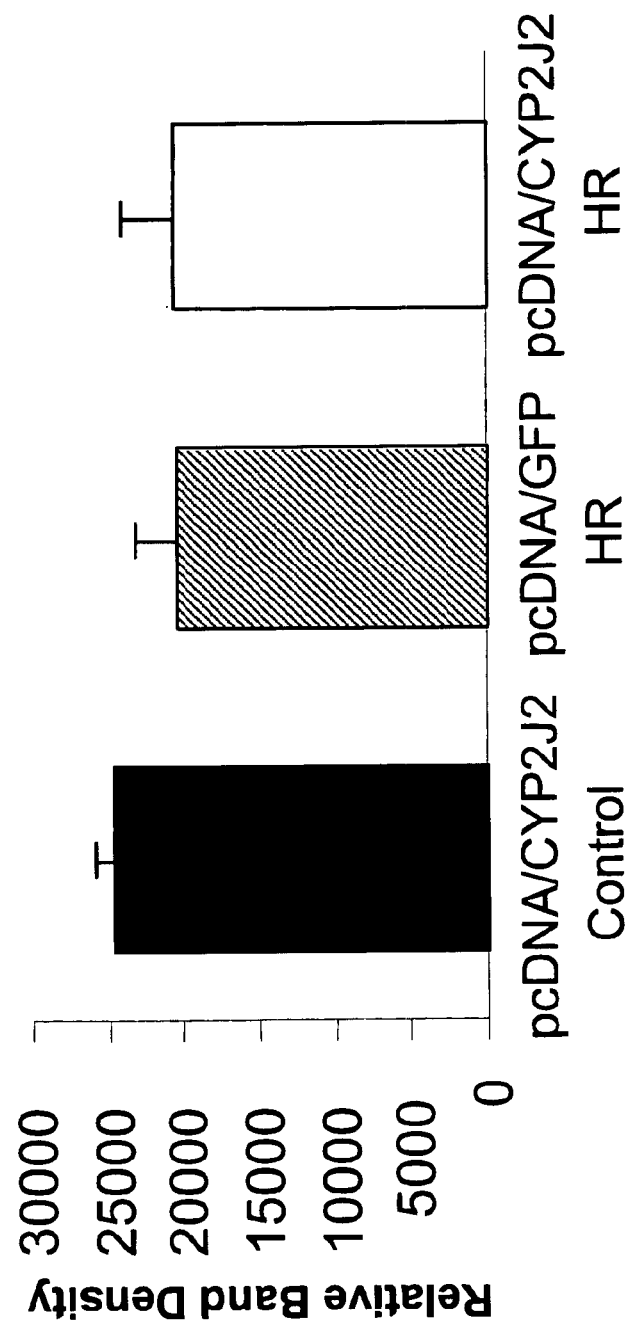
(FIG. 10C) Exposure of BAECs to hypoxia-reoxygenation did not change AT1 receptor expression either in GFP-transfected or CYP2J2-transfected cells. N=5 in each group.

Exposure of GFP-transfected BAECs to hypoxia-reoxygenation resulted in significantly lower eNOS expression and nitrite production compared to CYP2J2 transfected cells maintained under normoxic conditions (both $p<0.01$) (FIG. 10A and FIG. 10B). Endothelial NOS expression trended higher in CYP2J2-transfected cells exposed to hypoxia-reoxygenation (p=0.08) (FIG. 10A). Similarly, there was a trend toward increased nitrite production following hypoxia-reoxygenation in CYP2J2-transfected cells (p=0.20) (FIG. 10B). The inducible form of NOS was not detectable in any of the experimental groups. The angiotensin II type 1 receptor (AT1), which has been implicated in the pathogenesis of ischemic heart disease (Yang et al., 83 Circ. Res. 552–559 (1998)), was abundantly expressed in BAECs; however, there were no significant differences in AT1 expression following hypoxia-reoxygenation or after transfection with the CYP2J2 containing plasmid (FIG. 10C).

Discussion. In this EXAMPLE, we describe a new functional role for CYP2J2 and its eicosanoid products in limiting endothelial injury following exposure to hypoxia-reoxygenation. We demonstrate that CYP2J2 protein levels are markedly reduced following exposure of endothelial cells to hypoxia-reoxygenation and that maintenance of CYP2J2 levels attenuates the cellular injury. Given that endothelial injury is an important early event in the development of the atherosclerotic plaque and is associated with myocardial dysfunction in ischemic heart disease, we postulated that reduced CYP2J2 protein and/or activity is involved in the pathogenesis of these cardiovascular disorders.

The reduction in endothelial CYP2J2 protein expression following exposure to hypoxia-reoxygenation appears to be relatively selective for this protein. We observed that endothelial expression of the AT1 receptor remains unchanged following this stimulus. We and others have observed an upregulation of endothelial cell adhesion molecule expression (ICAM-1, ELAM-1, and E-selectin) following hypoxia-reoxygenation (Russell et al., 278 Am. J. Physiol. Gastrointest. Liver Physiol. G878–G885 (2000), Hess et al., 25 Stroke. 1463–1467 (1994)). In addition, it is well documented that interleukin-1, interleukin-6, and vascular endothelial growth factor are also induced in endothelial cells after hypoxia (Ala et al., 37 Agents Actions. 134–139 (1992), Marti et al., 156 Am. J. Pathol. 965–976 (2000)). Thus, our observations cannot be explained simply on the basis of a generalized, nonspecific reduction in protein synthesis and/or increase in protein degradation in the hypoxic BAECs.

It is interesting that eNOS expression and activity, like those of CYP2J2, are also decreased following exposure of endothelial cells to hypoxia-reoxygenation. One of the most important functions of the endothelium is nitric oxide production. Nitric oxide possess potent vasodilatory, anti-inflammatory, anti-thrombotic and anti-proliferative properties. Others have observed reduced eNOS expression and activity following ischemia-reperfusion injury (Giraldez et al., 272 J. Biol. Chem. 21420–21426 (1997), Shin et al., 271 J. Biol. Chem. 271: 11317–11324 (1996)). Importantly, maintenance of CYP2J2 protein levels significantly attenuated hypoxia-reoxygenation-induced injury in BAECs, but had only slight effects on eNOS expression and nitrite production suggesting that the mechanisms by which CYP2J2 exerts its protective effects in endothelial cells are largely independent of NOS.

In addition to the cyclooxygenase and lipoxygenase pathways, the P450 monooxygenase pathway is an important member of the cardiac arachidonic acid metabolic cascade (Wu et al., 272 J. Biol. Chem 12551 (1997)). This EXAMPLE demonstrates that BAECs metabolize radiolabeled arachidonic acid to EETs at appreciable rates, transfection of the endothelial cells with the CYP2J2 cDNA results in increased arachidonic acid epoxygenase activity, and this activity is reduced by the P450 inhibitor SKF-525A. Furthermore, recent gas chromatography/mass spectrometry analysis shows that EETs are endogenous constituents of control BAECs and that CYP2J2 transfection increases endogenous EET levels by approximately 30%. Together, these data establish a role for CYP2J2 in the biosynthesis of EETs from both exogenous and endogenous arachidonic acid pools in endothelial cells.

This EXAMPLE demonstrates that EETs likely mediate some of the cytoprotective effects of CYP2J2 transfection following hypoxia-reoxygenation. Thus, physiological concentrations of synthetic [11,12]-EET significantly attenuate cell injury and epoxide hydrolase inhibitors, which prolong the half life of endogenous EETs, are also cytoprotective. The combination of [11,12]-EET and epoxide hydrolase inhibitors have additive effects suggesting that hydrolysis may limit the biological effectiveness of the EETs. The magnitude of the effect of [11,12]-EET was generally less pronounced than that of CYP2J2 transfection. One possible explanation for this observation is that the cytoprotective effects of CYP2J2 in endothelial cells may involve EET-independent mechanisms. In this regard, we showed that CYP2J2 transfection significantly attenuates hypoxia-reoxygenation-induced increases in cellular $F_2$-isoprostanes and decreases endothelial superoxide anion formation. The relevance of reactive oxygen species generation and lipid peroxidation in the pathogenesis of ischemia-reperfusion injury is well established (Mathews et al., 16 Free Radic. Biol. Med. 763–70 (1994), Mehta et al., 5 J. Myocard. Ischemia.31–41 (1993)). Antioxidants are known to have beneficial cardiovascular functional effects following ischemia-reperfision (Mehta et al., 257 Am. J. Physiol. H1240–H1246 (1989), Meyer et al., 12 Can. J. Cardiol. 930–934 (1996)). Thus, the cytoprotective effects of CYP2J2 may be mediated, at least in part, by effects on oxidant generation.

In summary, this EXAMPLE demonstrates that exposure of cultured BAECs to hypoxia-reoxygenation results in cytotoxicity and reduced CYP2J2 protein expression. Transfection with the CYP2J2 cDNA, addition of synthetic [11, 12]-EET, or application of epoxide hydrolase inhibitors limits the hypoxia-reoxygenation-induced cellular injury. CYP2J2 transfection also attenuates the hypoxia-reoxygenation-induced increase in cellular $F_2$-isoprostanes, reduces superoxide anion formation, and tends to preserve eNOS expression/nitrite production. Together, these observations show that the mechanism for the cytoprotective effects of CYP2J2 in endothelial cells involves both EET-dependent and EET-independent pathways.

The foregoing description has been presented only for the purposes of illustration and is not intended to limit the invention to the precise form disclosed, but by the claims appended hereto.

We claim:

1. A method for reducing cell death from hypoxia-reoxygenation, comprising:

contacting a cell undergoing hypoxia reoxygenation with an effective amount of a composition of matter selected from the group consisting of epoxyeicosatrienoic acids (EETs), epoxyeicosatrienoic acid metabolic products, epoxyeicosatrienoic acid analogs, dihydroxycicosatrienoic acid analogs, and combinations thereof, wherein the epoxyeicosatrienoic acid analogs and dihydroxyeicosatrienoic acid analogs comprise an episulfide derivative; a sulfonamide derivative; and analog in which one or more EET olefins are removed; an analog in which an EET olefin is replaced with an acetylene group of a cyclopropane group; an analog in which an eopxide moiety is replaced with an oxitane or furane ring, wherein the composition reduces cell death in the cell undergoing hypoxia-reoxygenation.

2. The method of claim 1, wherein contacting a cell comprises administration of EETs, epoxyeicosatrienoic acid metabolic products, epoxyeicosatrienoic acid analogs, dihydroxyeicosatrienoic acid analogs, or combinations thereof to a subject, wherein the epoxyeicosatrienoic acid and dihydroxyeicosatrienoic acid analogs comprise an episulfide derivative; a sulfonamide derivative; an analog in which one or more EET olefins are removed; an analog in which an EET olefin is replaced with an acetylene group or a cyclopropane group; an analog in which an epoxide moiety is replaced with an oxitane or furan ring.

3. The method of claim 2, wherein the administration comprises producing EETs from a cytochrome P450 epoxygenase.

4. The method of claim 3, wherein the EET is [11,12]-EET, [14,15]-EET, or combinations thereof, and wherein the epoxyeicosatrienoic acid metabolic product is [11,12]-DHET.

5. The method of claim 3, wherein the cytochrome P450 epoxygenase is selected from the group consisting of CYP1A, CYP2B, CYP2C, CYP2E, and CYP2J enzymes.

6. The method of claim 5, wherein the CYP2J enzyme is a mammalian homologue of CYP2J2.

7. The method of claim 6, wherein the mammalian homologue is human CYP2J2.

8. The method of claim 6, wherein the mammalian homologue is rat CYP2J3 or mouse CYP2J5.

9. The method of claim 1, wherein the EET is [11,12]-EET or [14,15]-EET, and wherein the epoxyeicosatrienoic acid metabolic product is [11,12]-DHET.

10. The method of claim 1, wherein the cell is contacted with an effective amount of a composition of matter comprising epoxyeicosatrienoic acids (EETs).

11. The method of claim 1, wherein the cell is contacted with an effective amount of a composition of matter comprising epoxyeicosatrienoic acid metabolic products.

12. The method of claim 1, wherein the cell is contacted with an effective amount of a composition of matter comprising an episulfide derivative.

13. The method of claim 1, wherein the cell is contacted with an effective amount of a composition of matter comprising a sulfonamide derivative.

14. The method of claim 1, wherein the cell is contacted with an effective amount of a composition of matter comprising an analog in which one or more EET olefins are removed.

15. The method of claim 1, wherein the cell is contacted with an effective amount of a composition of matter comprising analogs in which the EET olefins are replaced with an acetylene group or a cyclopropane group.

16. The method of claim 1, wherein the cell is contacted with an effective amount of a composition of matter comprising an analog in which an epoxide moiety is replaced with an oxitane or furan ring.

17. The method of claim 14, wherein the analog in which one or more EET olefins are removed comprises an epoxyeicosadienoic acid, an epoxyeicosamonoenoic acid, or an epoxyeicosanoic acid.

18. The method of claim 2, wherein contacting a cell comprises administration of an effective amount of a composition of matter comprising epoxyeicosatrienoic acids (EETs) to the subject.

19. The method of claim 2, wherein contacting a cell comprises administration of an effective amount of a composition of matter comprising epoxyeicosatrienoic acid metabolic products to the subject.

20. The method of claim 2, wherein contacting a cell comprises administration of an effective amount of a composition of matter comprising an episulfide derivative to the subject.

21. The method of claim 2, wherein contacting a cell comprises administration of an effective amount of a composition of matter comprising a sulfonamide derivative to the subject.

22. The method of claim 2, wherein contacting a cell comprises administration of an effective amount of a composition of matter comprising an analog in which one or more EET olefins are removed to the subject.

23. The method of claim 2, wherein contacting a cell comprises administration of an effective amount of a composition of matter comprising an analog in which the EET olefins are replaced with an acetylene group or a cyclopropane group to the subject.

24. The method of claim 2, wherein contacting a cell comprises administration of an effective amount of a composition of matter comprising an analog in which an epoxide moiety is replaced with an oxitane or furan ring to the subject.

25. The method of claim 22, wherein the analogs in which one or more EET olefins are removed comprise an epoxyeicosadienoic acid, an epoxyeicosamonoenoic acid, or an epoxyeicosanoic acid.

* * * * *